(12) United States Patent
Vertatschitsch et al.

(10) Patent No.: US 10,195,464 B2
(45) Date of Patent: *Feb. 5, 2019

(54) SYSTEMS AND METHODS FOR TREATING A LUNG OF A PATIENT USING GUIDED RADIATION THERAPY OR SURGERY

(75) Inventors: Edward J. Vertatschitsch, Bellevue, WA (US); Steven C. Dimmer, Bellevue, WA (US); Timothy P. Mate, Bellevue, WA (US); Eric Meier, Bellevue, WA (US); Keith Seiler, Issaquah, WA (US); J. Nelson Wright, Mercer Island, WA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 1741 days.

This patent is subject to a terminal disclaimer.

(21) Appl. No.: 11/165,843

(22) Filed: Jun. 24, 2005

(65) Prior Publication Data
US 2006/0093089 A1    May 4, 2006

Related U.S. Application Data

(60) Provisional application No. 60/582,733, filed on Jun. 24, 2004.

(51) Int. Cl.
*A61B 5/05* (2006.01)
*A61N 5/10* (2006.01)
(Continued)

(52) U.S. Cl.
CPC ............ *A61N 5/1049* (2013.01); *A61B 34/25* (2016.02); *A61B 34/30* (2016.02);
(Continued)

(58) Field of Classification Search
USPC ....... 600/424, 426, 431, 433–436; 340/572.1
See application file for complete search history.

(56) References Cited

U.S. PATENT DOCUMENTS 3,967,161 A    6/1976 Lichtblau
4,023,167 A    5/1977 Wahlstrom
(Continued)

FOREIGN PATENT DOCUMENTS

JP      07313515 A    12/1995
JP    2001008947 A     1/2001
(Continued)

OTHER PUBLICATIONS

Sharp et al., "Prediction of Respiratory Tumour Motion for Real-Time Image-Guided Radiotherapy," Published Jan. 16, 2004; IPO Publishing Ltd; pp. 425-440.*
(Continued)

*Primary Examiner* — James Kish
(74) *Attorney, Agent, or Firm* — Perkins Coie LLP

(57) ABSTRACT

Systems and methods for treating a lung of a patient. One embodiment of a method comprises positioning a leadless marker in the lung of the patient relative to the target, and collecting position data of the marker. This method further comprises determining the location of the marker in an external reference frame outside of the patient based on the collected position data, and providing an objective output in the external reference frame that is responsive to movement of the marker. The objective output is provided at a frequency (i.e., periodicity) that results in a clinically acceptable tracking error. In addition, the objective output can also be provided at least substantially contemporaneously with collecting the position data used to determine the location of the marker.

21 Claims, 22 Drawing Sheets

(51) Int. Cl.
  *A61B 34/30* (2016.01)
  *A61B 34/00* (2016.01)
  *A61B 90/00* (2016.01)
(52) U.S. Cl.
  CPC . *A61B 2034/301* (2016.02); *A61B 2090/3958* (2016.02); *A61N 5/107* (2013.01); *A61N 5/1067* (2013.01); *A61N 2005/1051* (2013.01)

(56) References Cited

U.S. PATENT DOCUMENTS

| | | |
|---|---|---|
| 4,114,601 A | 9/1978 | Abels |
| 4,123,749 A | 10/1978 | Hartmann |
| 4,127,110 A | 11/1978 | Bullara |
| 4,160,971 A | 7/1979 | Jones |
| 4,216,860 A | 8/1980 | Heimann |
| 4,222,374 A | 9/1980 | Sampson et al. |
| 4,260,990 A | 4/1981 | Lichtblau |
| 4,393,872 A | 7/1983 | Reznik et al. |
| 4,618,822 A | 10/1986 | Hansen |
| 4,633,250 A | 12/1986 | Anderson III et al. |
| 4,643,196 A | 2/1987 | Tanaka et al. |
| 4,696,287 A | 9/1987 | Hortmann et al. |
| 4,795,995 A | 1/1989 | Eccleston et al. |
| 4,799,495 A | 1/1989 | Hawkins et al. |
| 4,900,303 A | 2/1990 | Lemelson |
| 4,909,789 A | 3/1990 | Taguchi |
| 4,936,823 A | 6/1990 | Colvin et al. |
| 4,945,914 A | 8/1990 | Allen |
| 4,994,079 A | 2/1991 | Genese |
| 5,031,634 A | 7/1991 | Israel |
| 5,061,634 A | 11/1991 | Barnes |
| 5,095,224 A | 3/1992 | Renger |
| 5,099,845 A | 3/1992 | Besz et al. |
| 5,107,862 A | 4/1992 | Fabian |
| 5,142,292 A | 8/1992 | Chang |
| 5,152,776 A | 10/1992 | Pinchuk |
| 5,170,055 A | 12/1992 | Carroll et al. |
| 5,325,873 A | 7/1994 | Hirschi et al. |
| 5,353,804 A | 10/1994 | Kornberg et al. |
| 5,409,004 A | 4/1995 | Sloan |
| 5,423,334 A | 6/1995 | Jordan |
| 5,425,367 A | 6/1995 | Shapiro et al. |
| 5,425,382 A | 6/1995 | Golden et al. |
| 5,446,548 A | 8/1995 | Gerig et al. |
| 5,509,900 A | 4/1996 | Kirkman |
| 5,528,651 A | 6/1996 | Leksell et al. |
| 5,626,630 A | 5/1997 | Markowitz et al. |
| 5,638,819 A | 6/1997 | Manwaring |
| 5,651,043 A | 7/1997 | Tsuyuki et al. |
| 5,680,106 A | 10/1997 | Schrott et al. |
| 5,707,362 A | 1/1998 | Yoon |
| 5,707,390 A | 1/1998 | Bonutti |
| 5,711,299 A | 1/1998 | Manwaring |
| 5,727,552 A | 3/1998 | Ryan |
| 5,735,795 A | 4/1998 | Young |
| 5,748,767 A | 5/1998 | Raab |
| 5,754,623 A | 5/1998 | Seki |
| 5,757,881 A | 5/1998 | Hughes |
| 5,764,052 A | 6/1998 | Renger |
| 5,769,861 A | 6/1998 | Vilsmeier |
| 5,810,851 A | 9/1998 | Yoon |
| 5,815,076 A | 9/1998 | Herring |
| 5,840,148 A | 11/1998 | Campbell et al. |
| 5,868,673 A | 2/1999 | Vesely |
| 5,879,297 A | 3/1999 | Haynor et al. |
| 5,879,357 A | 3/1999 | Heaton et al. |
| 5,910,144 A | 6/1999 | Hayashi |
| 5,928,137 A | 7/1999 | Green |
| 5,951,481 A | 9/1999 | Evans |
| 5,957,934 A | 9/1999 | Rapoport |
| 5,989,265 A | 11/1999 | Bouquet |
| 6,026,818 A | 2/2000 | Blair |
| 6,059,734 A | 5/2000 | Yoon |
| 6,061,644 A | 5/2000 | Leis |
| 6,067,465 A | 5/2000 | Foo et al. |
| 6,076,008 A | 6/2000 | Bucholz |
| 6,081,238 A | 6/2000 | Alicot |
| 6,082,366 A | 7/2000 | Andra |
| 6,144,875 A | 11/2000 | Schweikard et al. |
| 6,161,009 A | 12/2000 | Skurdal et al. |
| 6,198,963 B1 | 3/2001 | Haim et al. |
| 6,246,900 B1 | 6/2001 | Cosman et al. |
| 6,307,473 B1 | 10/2001 | Zampini et al. |
| 6,325,758 B1 | 12/2001 | Carol et al. |
| 6,353,655 B1 | 3/2002 | Siochi |
| 6,359,959 B1 | 3/2002 | Butler et al. |
| 6,363,940 B1 | 4/2002 | Krag |
| 6,371,379 B1 | 4/2002 | Dames et al. |
| 6,377,162 B1 | 4/2002 | Delestienne et al. |
| 6,381,485 B1 | 4/2002 | Hunter et al. |
| 6,385,286 B1 | 5/2002 | Fitchard et al. |
| 6,385,288 B1 | 5/2002 | Kanematsu |
| 6,393,096 B1 | 5/2002 | Carol et al. |
| 6,405,072 B1 | 6/2002 | Cosman |
| 6,416,520 B1 | 7/2002 | Kynast et al. |
| 6,994,712 B1 | 11/2002 | Fisher et al. |
| 6,501,981 B1 | 12/2002 | Schweikard et al. |
| 6,510,199 B1 | 1/2003 | Hughes et al. |
| 6,535,756 B1 | 3/2003 | Simon et al. |
| 6,650,930 B2 | 11/2003 | Ding |
| 6,662,036 B2 | 12/2003 | Cosman |
| 6,675,810 B2 | 1/2004 | Krag |
| 6,698,433 B2 | 3/2004 | Krag |
| 6,702,780 B1 | 3/2004 | Gilboa et al. |
| 6,812,842 B2 | 11/2004 | Dimmer |
| 6,822,570 B2 | 11/2004 | Dimmer et al. |
| 6,838,990 B2 | 1/2005 | Dimmer et al. |
| 6,882,947 B2 | 4/2005 | Levin |
| 6,918,919 B2 | 7/2005 | Krag |
| 6,934,356 B1 | 8/2005 | Satheesan |
| 6,937,696 B1 | 8/2005 | Mostafavi |
| 6,961,405 B2 * | 11/2005 | Scherch .................. 378/65 |
| 6,977,504 B2 | 12/2005 | Wright et al. |
| 6,993,112 B2 | 1/2006 | Hesse |
| 6,999,555 B2 | 2/2006 | Morf |
| 7,026,927 B2 | 4/2006 | Wright et al. |
| 7,027,707 B2 | 4/2006 | Imaki |
| 7,077,842 B1 | 7/2006 | Cosman |
| 7,142,905 B2 | 11/2006 | Slayton |
| 7,154,991 B2 | 12/2006 | Earnst |
| 7,206,626 B2 | 4/2007 | Quaid |
| 7,206,627 B2 | 4/2007 | Abovitz |
| 7,213,009 B2 | 5/2007 | Pestotnik |
| 7,221,733 B1 | 5/2007 | Takai |
| 7,247,160 B2 | 7/2007 | Seiler et al. |
| 7,280,863 B2 * | 10/2007 | Shachar .................. 600/424 |
| 7,289,599 B2 | 10/2007 | Seppi |
| 7,289,839 B2 | 10/2007 | Dimmer et al. |
| 7,318,805 B2 | 1/2008 | Schweikard et al. |
| 7,447,643 B1 | 11/2008 | Olson |
| 8,079,964 B2 | 8/2009 | Reichel et al. |
| 7,606,405 B2 | 10/2009 | Sawyer |
| 9,283,053 B2 | 3/2016 | Mayse et al. |
| 2001/0029509 A1 | 10/2001 | Smith et al. |
| 2002/0049362 A1 | 4/2002 | Ding |
| 2002/0065455 A1 | 5/2002 | Ben-Haim et al. |
| 2002/0065461 A1 | 5/2002 | Cosman |
| 2002/0165443 A1 | 11/2002 | Mori |
| 2002/0193685 A1 | 12/2002 | Mate et al. |
| 2003/0002621 A1 | 1/2003 | Hughes |
| 2003/0023161 A1 | 1/2003 | Govari |
| 2003/0052785 A1 | 3/2003 | Gisselberg et al. |
| 2003/0070682 A1 | 4/2003 | Wilson et al. |
| 2003/0088178 A1 | 5/2003 | Owens |
| 2003/0125622 A1 * | 7/2003 | Schweikard et al. ......... 600/437 |
| 2003/0153829 A1 | 8/2003 | Sarin |
| 2003/0192557 A1 | 10/2003 | Krag |
| 2003/0206610 A1 | 11/2003 | Collins |
| 2003/0206614 A1 | 11/2003 | Kendrick |
| 2003/0212412 A1 | 11/2003 | Dillard et al. |
| 2004/0019274 A1 | 1/2004 | Galloway |
| 2004/0068182 A1 | 4/2004 | Misra |
| 2004/0096033 A1 | 5/2004 | Seppi |

(56) References Cited

U.S. PATENT DOCUMENTS

| | | |
|---|---|---|
| 2004/0116804 A1 | 6/2004 | Mostafavi |
| 2004/0122308 A1 | 6/2004 | Ding |
| 2004/0122311 A1 | 6/2004 | Cosman |
| 2004/0123871 A1 | 7/2004 | Wright et al. |
| 2004/0124105 A1 | 7/2004 | Seiler et al. |
| 2004/0125916 A1 | 7/2004 | Herron |
| 2004/0127787 A1 | 7/2004 | Dimmer |
| 2004/0133101 A1 | 7/2004 | Mate et al. |
| 2004/0138555 A1 | 7/2004 | Krag |
| 2004/0162574 A1 | 8/2004 | Viola |
| 2004/0176931 A1 | 9/2004 | Wright |
| 2005/0059884 A1 | 3/2005 | Krag |
| 2005/0059887 A1 | 3/2005 | Mostafavi |
| 2005/0077459 A1 | 4/2005 | Engler |
| 2005/0151649 A1 | 7/2005 | Wright |
| 2005/0154280 A1 | 7/2005 | Wright |
| 2005/0154284 A1 | 7/2005 | Wright |
| 2005/0154293 A1 | 7/2005 | Gisselberg et al. |
| 2005/0251111 A1 | 11/2005 | Saito et al. |
| 2005/0261570 A1 | 11/2005 | Mate |
| 2006/0052694 A1 | 3/2006 | Phillips |
| 2006/0058548 A1 | 3/2006 | Meier |
| 2006/0063999 A1 | 3/2006 | Herron |
| 2006/0074301 A1 | 4/2006 | Meier |
| 2006/0074302 A1 | 4/2006 | Meier |
| 2006/0078086 A1 | 4/2006 | Riley |
| 2006/0079764 A1 | 4/2006 | Wright et al. |
| 2006/0100509 A1 | 5/2006 | Wright |
| 2007/0106108 A1 | 5/2007 | Hermann et al. |
| 2007/0161884 A1 | 7/2007 | Black |
| 2008/0226149 A1 | 9/2008 | Wischmann |
| 2010/0036241 A1 | 2/2010 | Mayse et al. |
| 2012/0101331 A1 | 4/2012 | Gilad et al. |

FOREIGN PATENT DOCUMENTS

| | | |
|---|---|---|
| JP | 2004154548 A | 6/2004 |
| WO | 9608208 A1 | 3/1996 |
| WO | WO 9712553 | 4/1997 |
| WO | WO 9830166 | 7/1998 |
| WO | WO 9840026 | 9/1998 |
| WO | WO 9838908 | 11/1998 |
| WO | WO 9927839 | 6/1999 |
| WO | WO 9930182 | 6/1999 |
| WO | WO 9933406 | 7/1999 |
| WO | WO 9940869 | 8/1999 |
| WO | WO 9958044 | 11/1999 |
| WO | WO 9958065 | 11/1999 |
| WO | WO-00/38579 | 7/2000 |
| WO | WO-00/51514 | 9/2000 |
| WO | WO 0065989 | 11/2000 |
| WO | WO 0239917 | 5/2002 |
| WO | WO 0239918 | 5/2002 |
| WO | WO 3053270 | 7/2002 |
| WO | 03053270 A2 | 7/2003 |
| WO | 05020925 A2 | 3/2005 |
| WO | 05067563 A2 | 7/2005 |

OTHER PUBLICATIONS

Wen, Jie. "Electromagnetic Tracking for Medical Imaging." Washington University in St. Lious. Jan. 2010. pp. 1-82.*

European Search Report for EP05763751; Applicant: Calypso Medical, Inc.; dated Sep. 18, 2008; 5 pgs; European Patent Office.

European Search Report for EP05763751; Applicant: Calypso Medical, Inc.; dated Feb. 21, 2008; 6 pgs; European Patent Office.

PCT International Search Report and Written Opinion for PCT/US05/22568; Applicant: Calypso Medical Technologies, Inc.; dated Feb. 26, 1007; 7 pgs.

Beyer, Thomas et al., "Dual-modality PET/CT Imaging: the effect of respiratory motion on combined image quality in clinical oncology," European Journal of Nuclear Medicine and Molecular Imagining 30.4 (2003): pp. 588-596.

Low, Daniel A. et al., "A method for reconstruction of four-dimensional synchronized CT scans acquired during free breathing," Medical Physics 30.6 (2003), pp. 1254-1263.

Seiler, P. G. et al., "A Novel Tracking Technique for the Continuous Precise Measurement of Turmour Positions in Conformal Therapy," Jun. 7, 2000, IOP Publishing Ltd., Phys. Med. Biol., vol. 45, pp. N103-N110.

Seppenwoolde et al., "Precise and Real-Time Measurement of 3D Tumor Motion in Lung due to Breathing and Heartbeat, Measured During Radiotherapy," Int. J. Radiant. Oncol. Biol. Phys. Jul. 15, 2002, 53, pp. 822-834.

Wolthaus, J. W. H. et al., "Fusion of Respiration-Correlated PET and CT Scans: Correlated Lung Tumour Motion in Anatomical and Functional Scans," Physics in Medicine and Biology 50.7 (205); p. 1569.

* cited by examiner

SYSTEMS AND METHODS FOR TREATING A LUNG OF A PATIENT USING GUIDED RADIATION THERAPY OR SURGERY

CROSS REFERENCE TO RELATED APPLICATIONS

This application claims the benefit of U.S. Provisional Application No. 60/582,733 filed on Jun. 24, 2004, which is herein incorporated by reference in its entirety.

TECHNICAL FIELD

This invention relates generally to systems and method for accurately locating and tracking a target in a lung of patient.

BACKGROUND OF THE INVENTION

Lung cancer is a disease that begins in the cells of the lungs. In general, there are two main categories of lung cancer: non-small cell lung cancer and small cell lung cancer. Non-small cell lung cancer may be treated using surgery, radiation, and/or chemotherapy. Because lung cancer varies from person to person, no single treatment may be effective for all patients. Typical surgeries for treating lung cancer include lobectomy (removing an entire lobe of a lung), pneumonectomy (removing an entire lung), and wedge or segmental resection (removing a small part of a lung). Surgery is generally not used if the cancer has spread to both lungs, other structures in the chest, the lymph nodes, or other organs. Surgery is also not used to treat tumors at central locations of the lung in which removal is not possible or in the case of small cell lung cancers. Surgery, therefore, is not a viable option for many patients. Surgical treatments may also result in complications with anesthesia or infection, and surgical treatments may have long, painful recovery periods.

Radiation therapy has become a significant and highly successful process for treating lung cancer, brain cancer and many other types of localized cancers. Radiation therapy is particularly useful for treating centrally located tumors and/or small cell tumors that cannot be removed surgically. Radiation therapy can be used as a curative treatment or as a palliative treatment when a cure is not possible. Additionally, surgery and chemotherapy can be used in combination with radiation therapy.

Radiation therapy procedures generally involve (a) a planning process to determine the parameters of the radiation (e.g., dose, shape, etc.), (b) a patient set-up process to position the target at a desired location relative to the radiation beam, (c) radiation sessions to irradiate the cancer, and (d) qualification processes to assess the efficacy of the radiation sessions. Many radiation therapy procedures have several radiation sessions over a period of approximately 5-45 days. Recent advances in radiation therapy, such as three-dimensional conformal external beam radiation, intensity modulated radiation therapy (IMRT), stereotactic radiosurgery and brachytherapy, provide effective treatments for cancer. These newer treatment modalities are often more effective than previous radiation therapies because they can deliver very high doses of radiation to the tumor.

To further improve the treatment of localized cancers with radiotherapy, it would be desirable to increase the radiation dose because higher doses are more effective at destroying most cancers. Increasing the radiation dose, however, also increases the potential for complications to healthy tissues.

The efficacy of radiation therapy accordingly depends on both the total dose of radiation delivered to the tumor and the dose of radiation delivered to normal tissue adjacent to the tumor. To protect the normal tissue adjacent to the tumor, the radiation should be prescribed to a tight treatment margin around the target to avoid irradiating healthy tissue. For example, the treatment margin for lung cancer should be selected to avoid irradiating healthy lung tissue. Therefore, it is not only desirable to increase the radiation dose delivered to the tumor, but it also desirable to mitigate the volume of healthy tissue subject to radiation and the dose of radiation delivered to such healthy tissue.

One difficulty of radiation therapy is compensating for movement of the target within the patient either during or between radiation sessions. This is particularly true in the case of central tumors. For example, tumors in the lungs move significant distances during radiation sessions because of respiration and cardiac functions (e.g., heartbeats and vasculature constriction/expansion). To compensate for such movement, the treatment margins are generally larger than desired so that the tumor does not move out of the treatment volume. This is not a desirable solution because the larger treatment margins may cause more normal tissue to be irradiated.

Another challenge in radiation therapy is accurately aligning the tumor with the isocenter of the radiation beam. Current setup procedures generally align external reference markings on the patient with visual alignment guides for the radiation delivery device. For an example, a tumor is first identified within the patient using an imaging system (e.g., X-ray, computerized tomography (CT), magnetic resonance imaging (MRI), or ultrasound system), and then the approximate location of a tumor in the body is aligned with two or more alignment points on the exterior of the patient. During setup, the external marks are aligned with a reference frame of the radiation delivery device to position the treatment target within the patient at the beam isocenter of the radiation beam (also referenced herein as the machine isocenter). Conventional setup procedures using external marks are generally inadequate because the target may move relative to the external marks between the patient planning procedure and the treatment session and/or during the treatment session. As such, the target may be offset from the machine isocenter even when the external marks are at their predetermined locations for positioning the target at the machine isocenter. Reducing or eliminating such an offset is desirable because any initial misalignment between the target and the radiation beam will cause normal tissue to be irradiated. Moreover, if the target moves during treatment because of respiration or cardiac functions, any initial misalignment will likely further exacerbate irradiation of normal tissue. Thus, the day-by-day and moment-by-moment changes in radiation treatment setup and target motion have posed significant challenges for increasing the radiation dose applied to patients.

Figure 1:
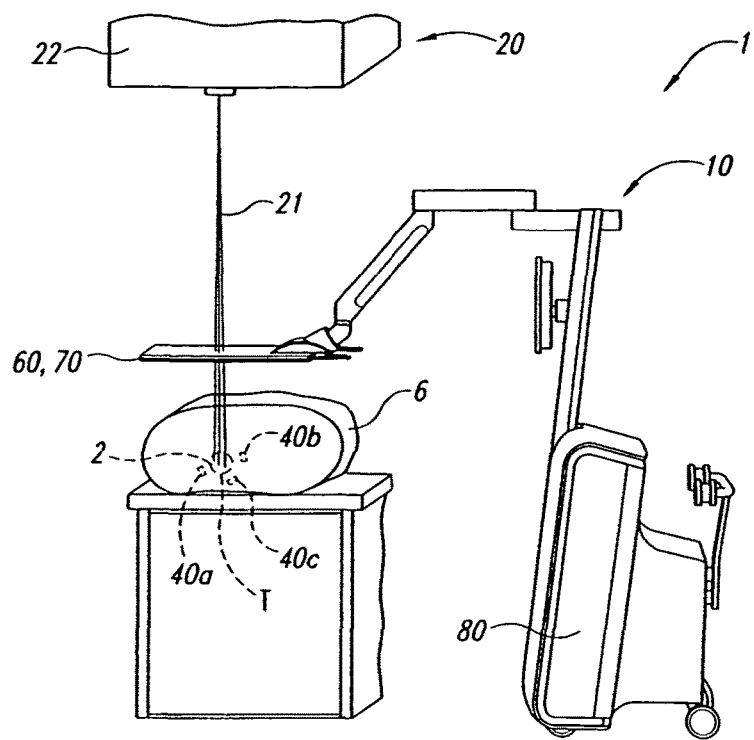
FIG. 1 is a side elevation view of a tracking system for use in localizing and monitoring a target in accordance with an embodiment of the present invention. Excitable markers are shown implanted in or adjacent to a target in a lung of the patient.

In the drawings, identical reference numbers identify similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION

In the following description, certain specific details are set forth in order to provide a thorough understanding of various embodiments of the invention. However, one skilled in the relevant art will recognize that the invention may be practiced without one or more of these specific details, or with other methods, components, materials, etc. In other instances, well-known structures associated with target locating and tracking systems have not been shown or described in detail to avoid unnecessarily obscuring descriptions of the embodiments of the invention.

Unless the context requires otherwise, throughout the specification and claims which follow, the word "comprise" and variations thereof, such as, "comprises" and "comprising" are to be construed in an open, inclusive sense that is as "including, but not limited to."

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Further more, the particular features, structures, or characteristics may be combined in any suitable manner in one or more embodiments.

The headings provided herein are for convenience only and do not interpret the scope or meaning of the claimed invention.

A. Overview

FIGS. 1-28 illustrate a system and several components for locating, tracking and monitoring a target within a lung of a patient in accordance with embodiments of the present invention. The system and components guide radiation therapy to more effectively treat the target. Several of the components described below with reference to FIGS. 1-28 can also be used to treat targets in other parts of the body in accordance with other aspects of the present invention. Additionally, like reference numbers refer to like components and features throughout the various figures.

One aspect of the invention is directed toward methods for treating a target in a lung of a patient. One embodiment of such a method comprises positioning a leadless marker in the lung of the patient relative to the target, and collecting position data of the marker. This method further comprises determining the location of the marker in an external reference frame based on the collected position data, and providing an objective output in the external reference frame that is responsive to movement of the marker. The objective output is provided at a frequency (i.e., periodicity) that adequately tracks the location of the target in real time within a clinically acceptable tracking error range. In addition, the objective output can also be provided at least substantially contemporaneously with collecting the position data used to determine the location of the marker.

Another embodiment of such a method includes placing a magnetic marker proximate to and/or within the lung of the patient relative to the target, positioning the target at a desired situs in a reference frame of the radiation beam by locating the magnetic marker relative to the reference frame, and moving the patient according to the location of the magnetic marker in the reference frame. The magnetic marker has a transponder including a circuit configured to be energized by a wirelessly transmitted excitation energy and to wirelessly transmit a magnetic location signal in response to the excitation energy. The magnetic marker is located by (a) wirelessly delivering a pulsed magnetic field to energize the magnetic marker, (b) wirelessly transmitting a pulsed location signal from the magnetic marker to a location outside the patient, (c) sensing the pulsed location signal at a sensor located outside the patient, and (d) periodically calculating the location of the magnetic marker in the reference frame. The method can further include irradiating the patient with the radiation beam when the calculated location of the magnetic marker indicates that the target is at the desired situs in the reference frame.

Another embodiment of a method for tracking a target in a lung of a patient comprises placing a magnetic marker proximate to and/or within the lung of the patient relative to the target. The magnetic marker has a transponder including a circuit configured to be energized by a wirelessly transmitted excitation energy and to wirelessly transmit a magnetic location signal in response to the excitation energy. This embodiment of the method further includes wirelessly delivering a pulsed magnetic field to energize the magnetic marker, wirelessly transmitting a pulsed location signal from the magnetic marker to a location outside the patient, sensing the pulsed location signal at a sensor located outside the patient, and periodically calculating the location of the magnetic marker in the reference frame.

Other methods are directed to deploying a marker into or generally proximate to the lung of the patient. One embodiment of such a method comprises guiding a delivery device with a leadless marker through the patient to position the marker at a desired site relative to a target in or near the lung of the patient. The marker has a transponder configured to receive a wirelessly transmitted excitation energy and generate a wirelessly transmitted location signal in response to the excitation energy. This method further continues releasing the leadless marker at the desired site and securing the marker to the patient at the desired site. For example, the marker can be secured using a stent or other expandable device, a barb, a suture, and/or an adhesive.

Another aspect of the invention is directed to an apparatus for deploying a marker in a lung of the patient. One embodiment of such an apparatus comprises an elongated body having a distal section configured to pass through a passageway in a lung of the patient and a leadless marker having a transponder. The leadless marker is releasably supported by the body at the distal section. The apparatus further includes a deployment mechanism at the distal section, and the deployment mechanism is configured to release the marker from the distal section of the body. In further embodiments, the apparatus can further comprise a steering mechanism configured to direct the distal section. For example, the steering mechanism can comprise a wire having a distal end attached to one side of the distal section of the body and a proximal section axially moveable relative to the body to flex the distal section. In still further embodiments, the transponder in the leadless marker comprises a magnetic transponder having a circuit configured to be energized by a wirelessly transmitted magnetic excitation energy and to wirelessly transmit a magnetic location signal in response to the magnetic excitation energy.

Another aspect of the invention is directed to a marker for implantation into a patient. One embodiment of such a marker comprises a capsule, a transponder in the capsule, and an anchor attached to the capsule. The transponder includes a circuit configured to be energized by a wirelessly transmitted excitation energy and to wirelessly transmit a magnetic location signal in response to the excitation energy. The anchor comprises an expandable member that moves between a stored position having a first radius and a deployed position having a second radius greater than the first radius.

Another embodiment of a marker comprises a marker section configured to be localized and an anchor attached to the marker section. The anchor comprises an expandable member that moves between a stored position having a first size and a deployed position having a second size greater than the first size. The anchor, for example, can be a stent, an umbrella-like expandable member, or an expandable cylindrical section.

Various embodiments of the invention are described in this section to provide specific details for a thorough understanding and enabling description of these embodiments. A person skilled in the art, however, will understand that the invention may be practiced without several of these details, or that additional details can be added to the invention. Where context permits, singular or plural terms may also include the plural or singular term, respectively. Moreover, unless the word "or" is expressly limited to mean only a single item exclusive from other items in reference to a list of at least two items, then the use of "or" in such a list is to be interpreted as including (a) any single item in the list, (b) all of the items in the list, or (c) any combination of the items in the list. Additionally, the term "comprising" is used throughout to means including at least the recited feature(s) such that any greater number of the same features and/or types of other features or components are not precluded.

B. Guided Radiation Therapy Systems with Real Time Tracking Systems

Figure 2:
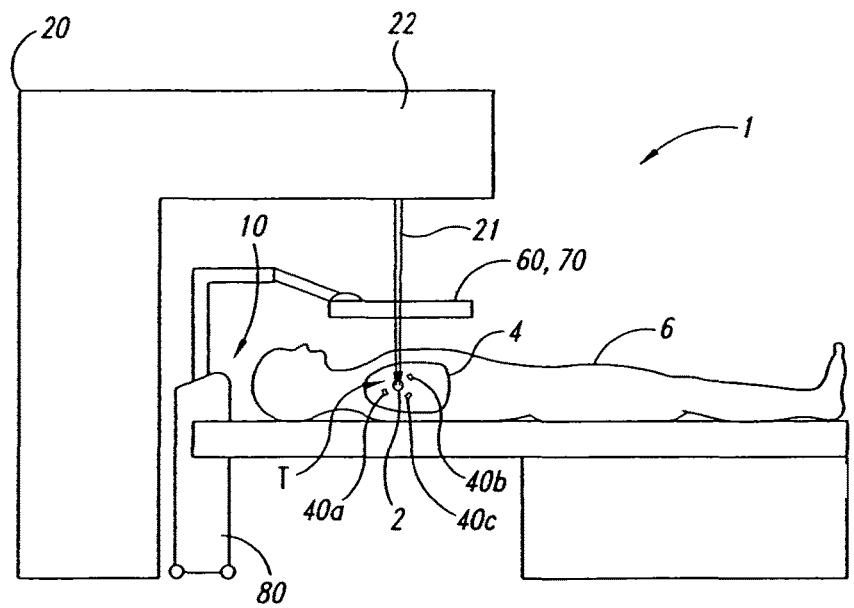
FIG. 2 is a schematic elevation view of the patient on a movable support table with the implanted markers.

FIGS. 1 and 2 illustrate various aspects of a radiation therapy system 1 for applying guided radiation therapy to a target 2 (e.g., a tumor) within a lung 4 of a patient 6. The radiation therapy system 1 has a tracking system and a radiation delivery device. The tracking system locates and tracks the actual position of the target 2 in real time during patient setup and while applying ionizing radiation to the target from the radiation delivery device. Thus, although the target 2 may move within the patient because of breathing, organ filling/emptying, cardiac functions or other internal movement as described above, the localization system 10 accurately tracks the motion of the target relative to an external reference outside of the patient to accurately deliver radiation within a small margin around the target. The localization system 10 can also monitor the configuration and trajectory of the marker to provide an early indicator of a change in the tumor without using ionizing radiation. Moreover, the localization system 10 continuously tracks the target and provides objective data (e.g., three-dimensional coordinates in an absolute reference frame) to a memory device, user interface, linear accelerator, and/or other device. The system 1 is described below in the context of guided radiation therapy for treating a tumor or other target in the lung of the patient, but the system can be used for tracking and monitoring other targets within the patient for other therapeutic and/or diagnostic purposes.

The radiation delivery source of the illustrated embodiment is an ionizing radiation device 20 (i.e., a linear accelerator). Suitable linear accelerators are manufactured by Varian Medical Systems, Inc. of Palo Alto, Calif.; Siemans Medical Systems, Inc. of Iselin, N.J.; Electa Instruments, Inc. of Iselin, N.J.; or Mitsubishi Denki Kabushik Kaisha of Japan. Such linear accelerators can deliver conventional single or multi-field radiation therapy, 3D conformal radiation therapy (3D CRT), intensity modulated radiation therapy (IMRT), stereotactic radiotherapy, and tomo therapy in conjunction with a variety of treatment planning software systems. The radiation delivery source 20 delivers a gated, contoured or shaped beam 21 of ionizing radiation from a movable gantry 22 to an area or volume at a known location in an external reference frame relative to the radiation delivery source 20. This point in space, referred to as a machine isocenter, is the point to which the ionizing radiation beam 21 is directed.

The tracking system includes a localization system 10 and one or more markers 40. The localization system 10 determines the actual location of the markers 40 in a three-dimensional reference frame, and the markers 40 are typically implanted within the patient 6. In the embodiment illustrated in FIGS. 1 and 2, more specifically, three markers identified individually as markers 40a-c are implanted in the lung 4 of the patient 6 at locations in or near the target 2. In other applications, a single marker, two markers, or more than three markers can be used depending upon the particular application. Two markers, for example, are highly desirable because the target can be located accurately, and also because relative displacement between the markers over time can be used to monitor marker migration in the patient. The markers 40 are desirably placed relative to the target 2 such that the markers 40 are at least substantially fixed relative to the target 2 (e.g., the markers move directly with the target or at least in direct proportion to the movement of the target). The relative positions between the markers 40 and a target isocenter T of the target 2 can be determined with respect to an external reference frame defined by a CT scanner or other type of imaging system during a treatment planning stage before placing the patient on the table. In the particular embodiment of the system 1 illustrated in FIGS. 1 and 2, the localization system 10 tracks the three-dimensional coordinates of the markers 40 in real time to an absolute external reference frame during the patient setup process and while irradiating the patient to mitigate collateral effects on adjacent healthy tissue and to ensure that the desired dosage is applied to the target.

1. General Operation of Selected Markers and Localization Systems

Figure 3:
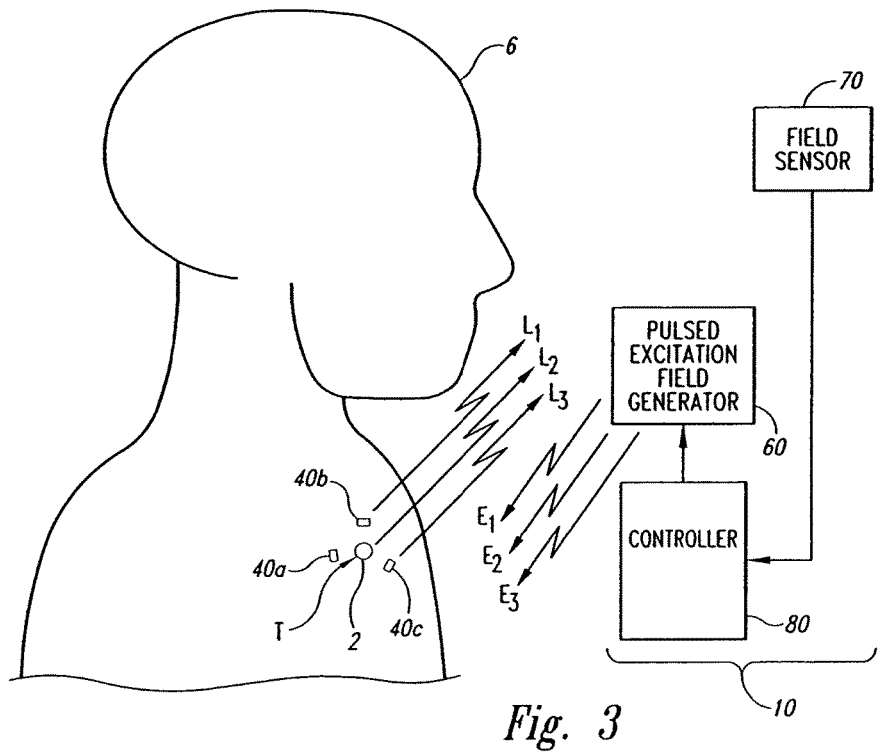
FIG. 3 is a side view schematically illustrating a localization system and a plurality of markers implanted in a lung of patient in accordance with an embodiment of the invention.

FIG. 3 is a schematic view illustrating the operation of an embodiment of the localization system 10 and markers 40a-c for treating a tumor or other target in the lung of the patient. The localization system 10 and the markers 40a-c are used to determine the location of the target 2 (FIGS. 1 and 2) before, during and after radiation sessions. More specifically, the localization system 10 determines the locations of the markers 40a-c and provides objective target position data to a memory, user interface, linear accelerator and/or other device in real time during setup, treatment, deployment, simulation, surgery, and/or other medical procedures. In one embodiment of the localization system, real time means that indicia of objective coordinates are provided to a user interface at (a) a sufficiently high refresh rate (i.e., frequency) such that pauses in the data are not humanly discernable and (b) a sufficiently low latency to be at least substantially contemporaneous with the measurement of the original signal. In other embodiments, real time is defined by higher frequency ranges and lower latency ranges for providing the objective data to a radiation delivery device, or in still other embodiments, real time is defined as providing objective data responsive to the location of the markers (e.g., at a periodicity or frequency that adequately tracks the location of the target in real time and/or at a latency that is at least substantially contemporaneous with obtaining position data of the markers).

The localization system 10 includes an excitation source 60 (e.g., a pulsed magnetic field generator), a sensor assembly 70, and a controller 80 coupled to both the excitation source 60 and the sensor assembly 70. The excitation source 60 generates an excitation energy to energize at least one of the markers 40a-c in the patient 6 (FIG. 1). The embodiment of the excitation source 60 shown in FIG. 3 produces a pulsed magnetic field at different frequencies. For example, the excitation source 60 can frequency multiplex the magnetic field at a first frequency $E_1$ to energize the first marker 40a, a second frequency $E_2$ to energize the second marker 40b, and a third frequency $E_3$ to energize the third marker 40c. In response to the excitation energy, the markers 40a-c generate location signals $L_{1-3}$ at unique response frequencies. More specifically, the first marker 40a generates a first location signal $L_1$ at a first frequency in response to the excitation energy at the first frequency $E_1$, the second marker 40b generates a second location signal $L_2$ at a second frequency in response to the excitation energy at the second frequency $E_2$, and the third marker 40c generates a third location signal $L_3$ at a third frequency in response to the excitation energy at the third frequency $E_3$. In an alternative embodiment with two markers, the excitation source generates the magnetic field at frequencies $E_1$ and $E_2$, and the markers 40a-b generate location signals $L_1$ and $L_2$, respectively.

The sensor assembly 70 can include a plurality of coils to sense the location signals $L_{1-3}$ from the markers 40a-c. The sensor assembly 70 can be a flat panel having a plurality of coils that are at least substantially coplanar relative to each other. In other embodiments, the sensor assembly 70 may be a non-planar array of coils.

The controller 80 includes hardware, software or other computer-operable media containing instructions that operate the excitation source 60 to multiplex the excitation energy at the different frequencies $E_{1-3}$. For example, the controller 80 causes the excitation source 60 to generate the excitation energy at the first frequency $E_1$ for a first excitation period, and then the controller 80 causes the excitation source 60 to terminate the excitation energy at the first frequency $E_1$ for a first sensing phase during which the sensor assembly 70 senses the first location signal $L_1$ from the first marker 40*a* without the presence of the excitation energy at the first frequency $E_1$. The controller 80 then causes the excitation source 60 to: (a) generate the second excitation energy at the second frequency $E_2$ for a second excitation period; and (b) terminate the excitation energy at the second frequency $E_2$ for a second sensing phase during which the sensor assembly 70 senses the second location signal $L_2$ from the second marker 40*b* without the presence of the second excitation energy at the second frequency $E_2$. The controller 80 then repeats this operation with the third excitation energy at the third frequency $E_3$ such that the third marker 40*c* transmits the third location signal $L_3$ to the sensor assembly 70 during a third sensing phase. As such, the excitation source 60 wirelessly transmits the excitation energy in the form of pulsed magnetic fields at the resonant frequencies of the markers 40*a*-*c* during excitation periods, and the markers 40*a*-*c* wirelessly transmit the location signals $L_{1-3}$ to the sensor assembly 70 during sensing phases. It will be appreciated that the excitation and sensing phases can be repeated to permit averaging of the sensed signals to reduce noise.

The computer-operable media in the controller 80, or in a separate signal processor, also includes instructions to determine the absolute positions of each of the markers 40*a*-*c* in a three-dimensional reference frame. Based on signals provided by the sensor assembly 70 that correspond to the magnitude of each of the location signals $L_{1-3}$, the controller 80 and/or a separate signal processor calculates the absolute coordinates of each of the markers 40*a*-*c* in the three-dimensional reference frame.

2. Real Time Tracking

The localization system 10 and markers 40 enable real time tracking of the target 2 relative to the machine isocenter or another external reference frame outside of the patient during treatment planning, set up, irradiation sessions, and at other times of the radiation therapy process. In many embodiments, real time tracking means collecting position data of the markers, determining the locations of the markers in an external reference frame (i.e., a reference frame outside the patient), and providing an objective output in the external reference frame responsive to the location of the marker. The objective output is provided at a frequency/periodicity that adequately tracks the target in real time, and/or a latency that is at least substantially contemporaneous with collecting the position data (e.g., within a generally concurrent period of time).

For example, several embodiments of real time tracking are defined as determining the locations of the markers and calculating the location of the target relative to the machine isocenter at (a) a sufficiently high frequency/periodicity so that pauses in representations of the target location at a user interface do not interrupt the procedure or are readily discernable by a human, and (b) a sufficiently low latency to be at least substantially contemporaneous with the measurement of the location signals from the markers. Alternatively, real time means that the location system 10 calculates the absolute position of each individual marker 40 and/or the location of the target at a periodicity of approximately 1 ms to 5 seconds, or in many applications at a periodicity of approximately 10-100 ms, or in some specific applications at a periodicity of approximately 20-50 ms. In applications for user interfaces, for example, the periodicity can be 12.5 ms (i.e., a frequency of 80 Hz), 16.667 ms (60 Hz), 20 ms (50 Hz), and/or 50 ms (20 Hz). Additionally, real time tracking can further mean that the location system 10 provides the absolute locations of the markers 40 and/or the target 2 to a memory device, user interface, linear accelerator or other device within a latency of 10 ms to 5 seconds from the time the localization signals were transmitted from the markers 40. In more specific applications, the location system generally provides the locations of the markers 40 and/or target 2 within a latency of about 20-50 ms. The location system 10 accordingly provides real time tracking to monitor the position of the markers 40 and/or the target 2 with respect to an external reference frame in a manner that is expected to enhance the efficacy of radiation therapy because higher radiation doses can be applied to the target and collateral effects to healthy tissue can be mitigated.

Alternatively, real time tracking can further mean that the location system 10 provides the absolute locations of the markers 40 and/or the target 2 to a memory device, user interface, linear accelerator or other device within a latency of 10 ms to 5 seconds from the time the localization signals were transmitted from the markers 40. In more specific applications, the location system generally provides the locations of the markers 40 and/or target 2 within a latency of about 20-50 ms. The location system 10 accordingly provides real time tracking to monitor the position of the markers 40 and/or the target 2 with respect to an external reference frame in a manner that is expected to enhance the efficacy of radiation therapy because higher radiation doses can be applied to the target and collateral effects to healthy tissue can be mitigated.

Alternatively, real-time tracking can further be defined by the tracking error. Measurements of the position of a moving target are subject to motion-induced error, generally referred to as a tracking error. According to aspects of the present invention, the localization system 10 and at least one marker 4 enable real time tracking of the target 2 relative to the machine isocenter or another external reference frame with a tracking error that is within clinically meaningful limits.

Tracking errors are due to two limitations exhibited by any practical measurement system, specifically (a) latency between the time the target position is sensed and the time the position measurement is made available, and (b) sampling delay due to the periodicity of measurements. For example, if a target is moving at 5 cm/s and a measurement system has a latency of 200 ms, then position measurements will be in error by 1 cm. The error in this example is due to latency alone, independent of any other measurement errors, and is simply due to the fact that the target has moved between the time its position is sensed and the time the position measurement is made available for use. If this exemplary measurement system further has a sampling periodicity of 200 ms (i.e., a sampling frequency of 5 Hz), then the peak tracking error increases to 2 cm, with an average tracking error of 1.5 cm.

For a real time tracking system to be useful in medical applications, it is desirable to keep the tracking error within clinically meaningful limits. For example, in a system for tracking motion of a tumor in a lung for radiation therapy, it may be desirable to keep the tracking error within 5 mm. Acceptable tracking errors may be smaller when tracking other organs for radiation therapy. In accordance with aspects of the present invention, real time tracking refers to measurement of target position and/or rotation with tracking errors that are within clinically meaningful limits.

The system described herein uses one or more markers to serve as registration points to characterize target location, rotation, and motion. In accordance with aspects of the invention, the markers have a substantially fixed relationship with the target. If the markers did not have a substantially fixed relationship with the target another type of tracking error would be incurred. This generally requires the markers to be fixed or implanted sufficiently close to the target in order that tracking errors be within clinically meaningful limits, thus, the markers may be placed in tissue or bone that exhibits representative motion of the target. For example, with respect to the prostate, tissue that is representative of the target's motion would include tissue in close proximity or adjacent to the prostate. Tissue adjacent to a target involving the prostate may include the prostate gland, the tumor itself, or tissue within a specified radial distance from the target. With respect to the prostate, tracking tissue that is a 5 cm radial distance from the target would provide representative motion that is clinically useful to the motion of the target. In accordance with alternative target tracking locations, the radial distance may be greater or lesser.

According to aspects of the present invention, the marker motion is a surrogate for the motion of the target. Accordingly, the marker is placed such that it moves in direct correlation to the target being tracked. Depending on the target being tracked, the direct correlation relationship between the target and the marker will vary. For example, in long bones, the marker may be place anywhere along the bone to provide motion that directly correlations to target motion in the bone. With respect to soft tissue that moves substantially in response to the bony anatomy, for example, the head and neck, the marker may be placed in a bite block to provide surrogate motion in direct correlation with target motion. With respect to soft tissue and as discussed in detail above, the target may be placed in adjacent soft tissue to provide a surrogate having direct correlation to target motion.

Figure 4:
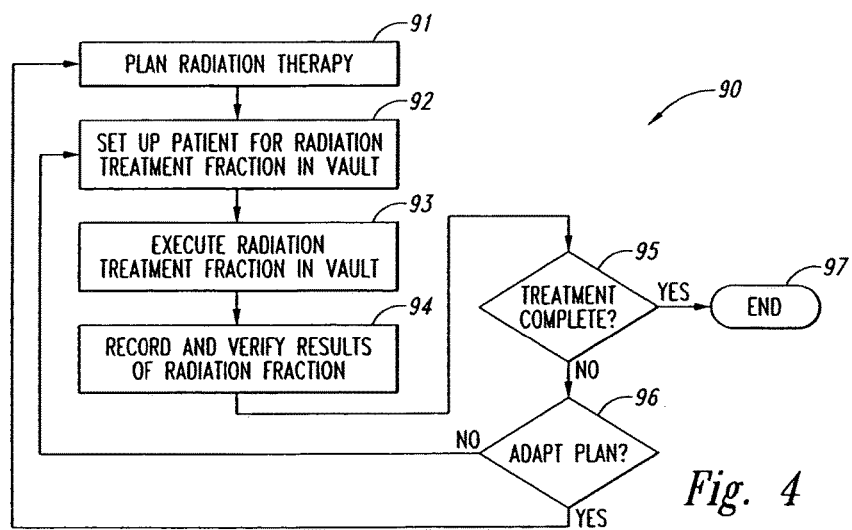
FIG. 4 is a flow diagram of an integrated therapy process that uses real time target tracking for radiation therapy to treat the lung of a patient in accordance with an embodiment of the invention.
Figure 5A:
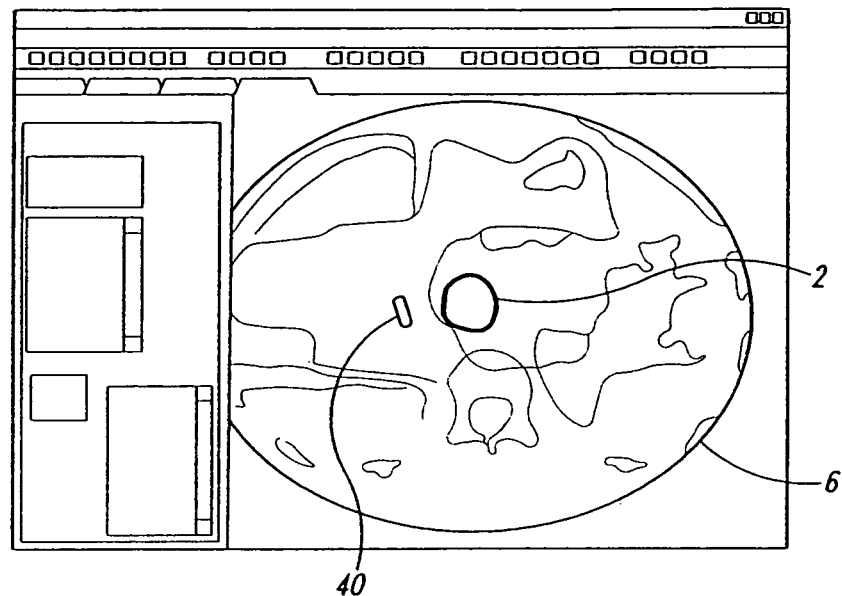
FIG. 5A is a representation of a CT image illustrating an aspect of a system and method for real time tracking of targets in radiation therapy and other medical applications.
Figure 5B:
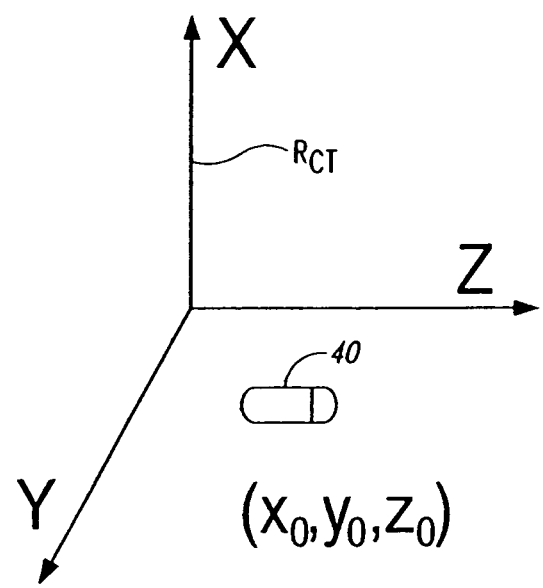
FIG. 5B is a diagram schematically illustrating a reference frame of a CT scanner.

FIG. 4 is a flow diagram illustrating several aspects and uses of real time tracking to monitor the location and the status of the target. In this embodiment, an integrated method 90 for radiation therapy includes a radiation planning procedure 91 that determines the plan for applying the radiation to the patient over a number of radiation fractions. The radiation planning procedure 91 typically includes an imaging stage in which images of a tumor or other types of targets are obtained using X-rays, CT, MRI, or ultrasound imaging. The images are analyzed by a person to measure the relative distances between the markers and the relative position between the target and the markers. FIG. 5A, for example, is a representation of a CT image showing a cross-section of the patient 6, the target 2, and a marker 40. Referring to FIG. 5B, the coordinates $(x_0, y_0, z_0)$ of the marker 40 in a reference frame $R_{CT}$ of the CT scanner can be determined by an operator. The coordinates of the tumor can be determined in a similar manner to ascertain the relative distance between the marker and the target.

The radiation planning procedure 91 can also include tracking the targets using the localization system 10 (FIG. 3) in an observation area separate from the imaging equipment. The markers 40 (FIG. 3) can be tracked to identify changes in the configuration (e.g., size/shape) of the target over time and to determine the trajectory of the target caused by movement of the target within the patient (e.g., simulation). For many treatment plans, the computer does not need to provide objective output data of the marker or target locations to a user in real time, but rather the data can be recorded in real time. Based on the images obtained during the imaging stage and the additional data obtained by tracking the markers after the imaging stage using the localization system 10 in a simulation procedure, a treatment plan is developed for applying the radiation to the target.

Figure 6:
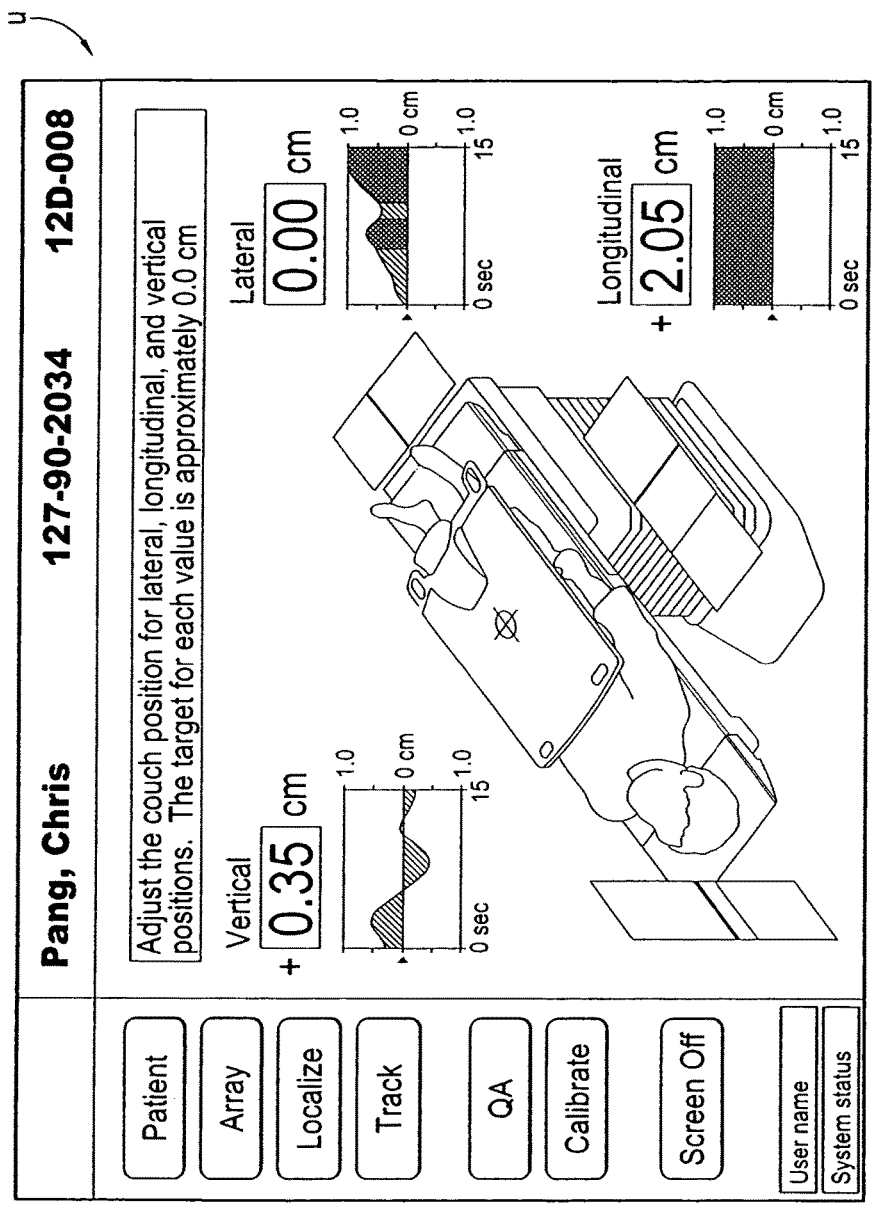
FIG. 6 is a screen shot of a user interface for displaying an objective output in accordance with an embodiment of the invention.

The localization system 10 and the markers 40 enable an automated patient setup process for delivering the radiation. After developing a treatment plan, the method 90 includes a setup procedure 92 in which the patient is positioned on a movable support table so that the target and markers are generally adjacent to the sensor assembly. As described above, the excitation source is activated to energize the markers, and the sensors measure the strength of the signals from the markers. The computer controller then (a) calculates objective values of the locations of the markers and the target relative to the machine isocenter, and (b) determines an objective offset value between the position of the target and the machine isocenter. Referring to FIG. 6, for example, the objective offset values can be provided to a user interface that displays the vertical, lateral and longitudinal positions of the target relative to a machine isocenter. One aspect of several embodiments of the localization system 10 is that the objective values are provided to the user interface or other device by processing the position data from the field sensor 70 in the controller 80 or other computer without human interpretation of the data received by the field sensor 70. If the offset value is outside of an acceptable range, the computer automatically activates the control system of the support table to move the tabletop relative to the machine isocenter until the target isocenter is coincident with the machine isocenter. The computer controller generally provides the objective output data of the offset to the table control system in real time as defined above. For example, because the output is provided to the radiation delivery device, it can be at a high rate (1-20 ms) and a low latency (10-20 ms). If the output data is provided to a user interface in addition to or in lieu of the table controller, it can be at a relatively lower rate (20-50 ms) and higher latency (50-200 ms).

In one embodiment, the computer controller also determines the position and orientation of the markers relative to the position and orientation of simulated markers. The locations of the simulated markers are selected so that the target will be at the machine isocenter when the real markers are at the selected locations for the simulated markers. If the markers are not properly aligned and oriented with the simulated markers, the support table is adjusted as needed for proper marker alignment. This marker alignment properly positions the target along six dimensions, namely X, Y, Z, pitch, yaw, and roll. Accordingly, the patient is automatically positioned in the correct position relative to the machine isocenter for precise delivery of radiation therapy to the target.

Figure 7:
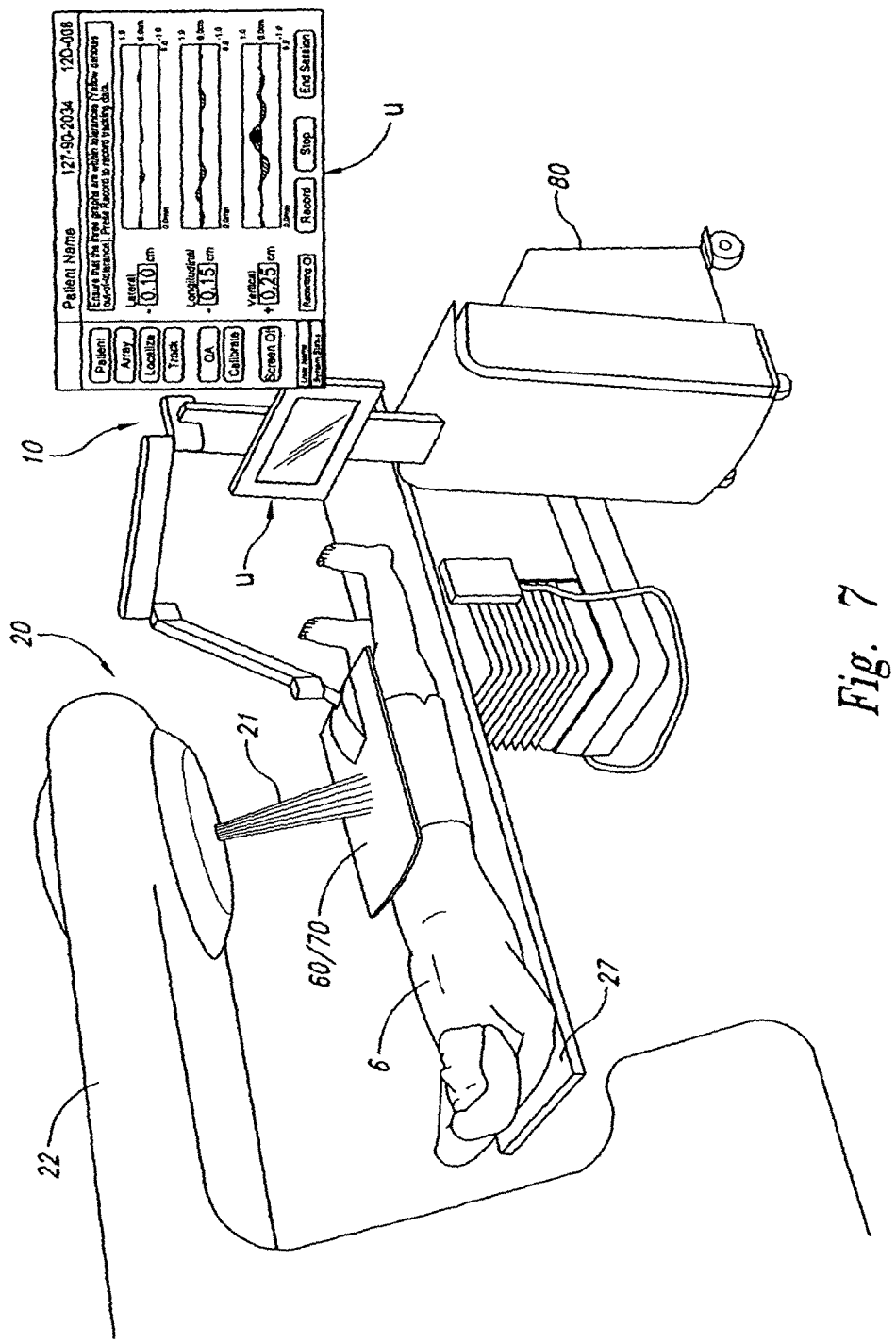
FIG. 7 is an isometric view of a radiation session in accordance with an embodiment of the invention.

Referring back to FIG. 4, the method 90 further includes a radiation session 93. FIG. 7 shows a further aspect of an automated process in which the localization system 10 tracks the target during the radiation session 93 and controls the radiation delivery device 20 according to the offset between target and the machine isocenter. For example, if the position of the target is outside of a permitted degree or range of displacement from the machine isocenter, the localization system 10 sends a signal to interrupt the delivery of the radiation or prevent initial activation of the beam. In another embodiment, the localization system 10 sends signals to automatically reposition a tabletop 27 and the patient 6 (as a unit) so that the target isocenter remains within a desired range of the machine isocenter during the radiation session 93 even if the target moves. In still another embodiment, the localization system 10 sends signals to activate the radiation only when the target is within a desired range of the machine isocenter (e.g., gated therapy). In the case of treating a target in the lung, one embodiment of gated therapy includes tracking the target during inspiration/expiration, having the patient hold his/her breath at the end of an inspiration/expiration cycle, and activating the beam 21 when the computer 80 determines that the objective offset value between the target and the machine isocenter is within a desired range. Accordingly, the localization system enables dynamic adjustment of the table 27 and/or the beam 21 in real time while irradiating the patient. This is expected to ensure that the radiation is accurately delivered to the target without requiring a large margin around the target.

The localization system provides the objective data of the offset and/or rotation to the linear accelerator and/or the patient support table in real time as defined above. For example, as explained above with respect to automatically positioning the patent support table during the setup procedure 92, the localization system generally provides the objective output to the radiation delivery device at least substantially contemporaneously with obtaining the position data of the markers. The objective output, for example, can be provided at a short periodicity (1-20 ms) and a low latency (10-20 ms) such that signals for controlling the beam 21 can be sent to the radiation delivery device 20 in the same time periods during a radiation session. In the case of terminating or activating the radiation beam, or adjusting the leafs of a beam collimator, it is generally desirable to maximize the frequency and minimize the latency. In some embodiments, therefore, the localization system may provide the objective output data of the target location and/or the marker locations at a periodicity of 10 ms or less and a latency of 10 ms or less.

The method 90 further includes a verification procedure 94 in which the real time objective output data from the radiation session 93 is compared to the status of the parameters of the radiation beam. For example, the target locations can be correlated with the beam intensity, beam position, and collimator configuration at corresponding time intervals during the radiation session 93. This correlation can be used to determine the dose of radiation delivered to discrete regions in and around the target. This information can also be used to determine the effects of radiation on certain areas of the target by noting changes in the target configuration or the target trajectory.

The method 90 can further include a first decision (Block 95) in which the data from the verification procedure 94 is analyzed to determine whether the treatment is complete. If the treatment is not complete, the method 90 further includes a second decision (Block 96) in which the results of the verification procedure are analyzed to determine whether the treatment plan should be revised to compensate for changes in the target. If revisions are necessary, the method can proceed with repeating the planning procedure 91. On the other hand, if the treatment plan is providing adequate results, the method 90 can proceed by repeating the setup procedure 92, radiation session 93, and verification procedure 94 in a subsequent fraction of the radiation therapy.

The localization system 10 provides several features, either individually or in combination with each other, that enhance the ability to accurately deliver high doses of radiation to targets within tight margins. For example, many embodiments of the localization system use leadless markers that are implanted in the patient so that they are substantially fixed with respect to the target. The markers accordingly move either directly with the target or in a proportional relationship to the movement of the target. As a result, internal movement of the target caused by respiration, organ filling, cardiac functions, or other factors can be identified and accurately tracked before, during and after medical procedures. Moreover, many aspects of the localization system 10 use a non-ionizing energy to track the leadless markers in an external, absolute reference frame in a manner that provides objective output. In general, the objective output is determined in a computer without having a human interpret data (e.g., images) while the localization system 10 tracks the target and provides the objective output. This significantly reduces the latency between the time when the position of the marker is sensed and the objective output is provided to a device or a user. For example, this enables an objective output responsive to the location of the target to be provided at least substantially contemporaneously with collecting the position data of the marker. The system also effectively eliminates inter-user variability associated with subjective interpretation of data (e.g., images).

In the embodiments discussed above, the markers 40 are described and shown as being subcutaneously implanted in or next to a target 2 to ensure that the markers will move with the target 2 within the patient. In an alternate embodiment, the markers can be surface-mounted to the exterior surface of the patient in addition to being implanted near the target 2. Such surface-mounted markers can be removably adhered to the patient with tape or another type of adhesive in a substantially fixed location.

Surface-mounted markers can be useful for monitoring the base-line girth (anterior-posterior and lateral dimensions) of the patient during a radiation treatment program. The base-line girth measurements, referred to as patient separations, can change over time because of the effects of chemo or radiotherapy. Such changes in the patient separations can invalidate the treatment plan because less tissue is available to attenuate the radiation beam. The controller 80 can detect the extent of change in the patient separations based on the measuring the relative distances between the surface-mounted markers. If the measured extent of change in the patient separations exceeds a predetermined limit, the controller 80 can send a warning message to redefine the treatment plan.

The surface-mounted markers can also be used to improve the patient setup procedures before and/or during the radiation therapy procedure. For example, the location of the surface markers can be used to calculate the Target Skin Distance or Source Skin Distance between the exterior skin of the patient and the linear actuator or the tabletop.

C. Specific Embodiments of Delivery Devices, Markers, and Localization Systems The following specific embodiments of delivery devices, markers, excitation sources, sensors and controllers provide additional details to implement the systems and processes described above with reference to FIGS. 1-7. The present inventors overcame many challenges to develop delivery devices, markers, and localization systems that accurately determine the location of a marker which (a) produces a wirelessly transmitted location signal in response to a wirelessly transmitted excitation energy, and (b) has a cross-section small enough to be implanted in or near the lung of a patient. Systems with these characteristics have several practical advantages, including (a) not requiring ionization radiation, (b) not requiring line-of-sight between the markers and sensors, and (c) effecting an objective measurement of a target's location and/or rotation. The following specific embodiments are described in sufficient detail to enable a person skilled in the art to make and use such a localization system for radiation therapy involving a tumor in the lung of the patient, but the invention is not limited to the following embodiments of delivery devices, markers, excitation sources, sensor assemblies and/or controllers.

1. Delivery Devices

Figure 8:
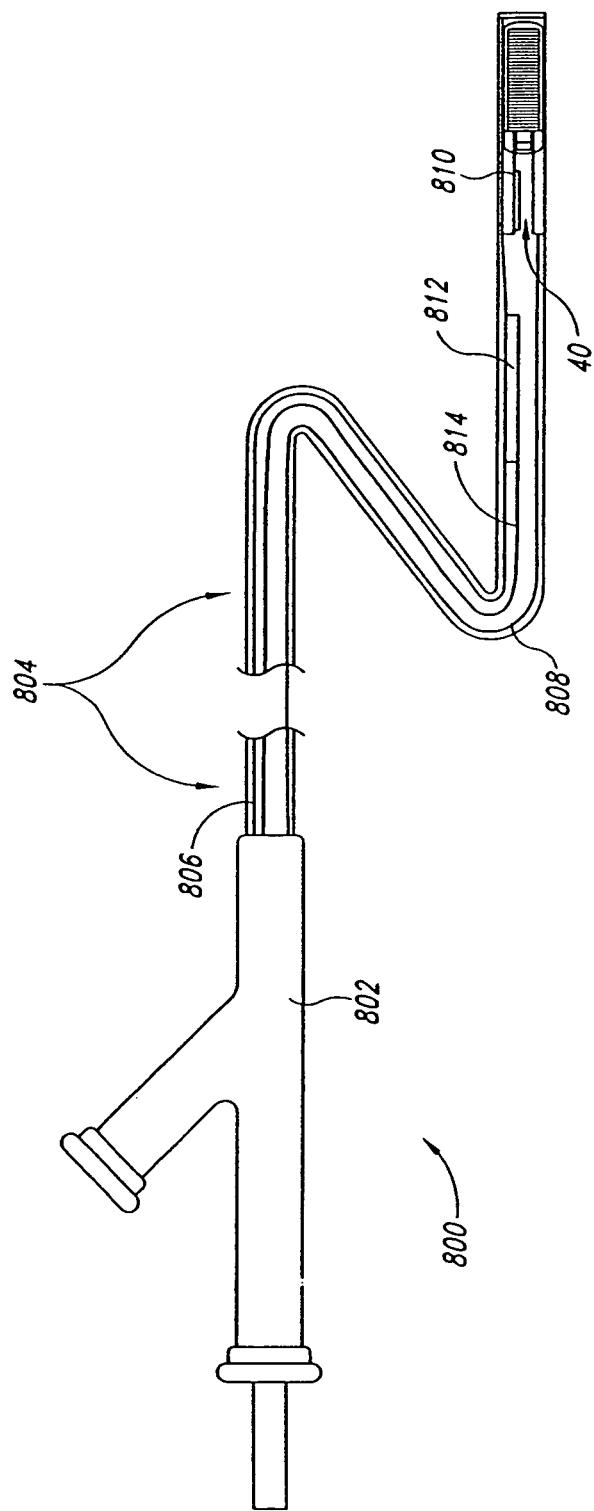
FIG. 8 is a cross-sectional view of a delivery device in accordance with an embodiment of the invention.

One aspect of several embodiments of the present invention is delivering or deploying the markers 40 into or at least proximate to a tumor located in the lung of the patient. FIG. 8 is a cross-sectional view of a delivery device 800 for deploying a marker 40 in the patient. The delivery device 800 can be a bronchoscope, catheter, or other device configured to pass through a lumen in the respiratory system of the patient. The delivery device 800 includes a handle 802 and an elongated body 804 attached to the handle 802. More specifically, the elongated body 804 includes a proximal section 806 at the handle 802 and a distal section 808 configured to pass through lumen in the respiratory system. In many embodiments, the distal section 808 of the elongated body 804 is flexible, but in other embodiments the entire elongated body can be flexible or rigid. The marker 40 is supported by the elongated body 804 at the distal section 808 for deployment into the patient. In several embodiments, the delivery device 800 further includes a deployment mechanism 810 that is operable from the handle 802 to release the marker 40 into the patient. The deployment mechanism 810 can be a push rod that pushes the marker 40 out of the distal section 808 of the elongated body 804. In an alternative embodiment, the deployment mechanism 810 can include a cannula and a stylet slidably received in the cannula. In this embodiment, the cannula and stylet are configured to move together to project distally beyond the distal section 808 of the elongated body 804, and then the cannula may be withdrawn proximally relative to the stylet to release the marker into the patient. Analogous embodiments of cannulas and stylets that can be used with the delivery device 800 are described below with respect to FIG. 9.

The delivery device 800 further includes a steering mechanism 812 that is operable from the handle 802. The steering mechanism 812 can include an attachment point at the distal section 808 and a slidable member 814 configured to move longitudinally relative to the elongated body 804. Longitudinal movement of the slidable member 814 flexes the distal section 808 in a manner that steers the delivery device 800 through bends and bifurcations in the lumen of the respiratory system. In other embodiments, the steering mechanism comprises a flexible support element and a flexible control element attached to the flexible support element such that tension applied to the control element flexes the flexible support element. Suitable steering mechanisms are set forth in U.S. Pat. No. 6,702,780 and U.S. Patent Application Publication No. US 2003/0208101 A1, both of which are incorporated herein by reference.

Figure 9:
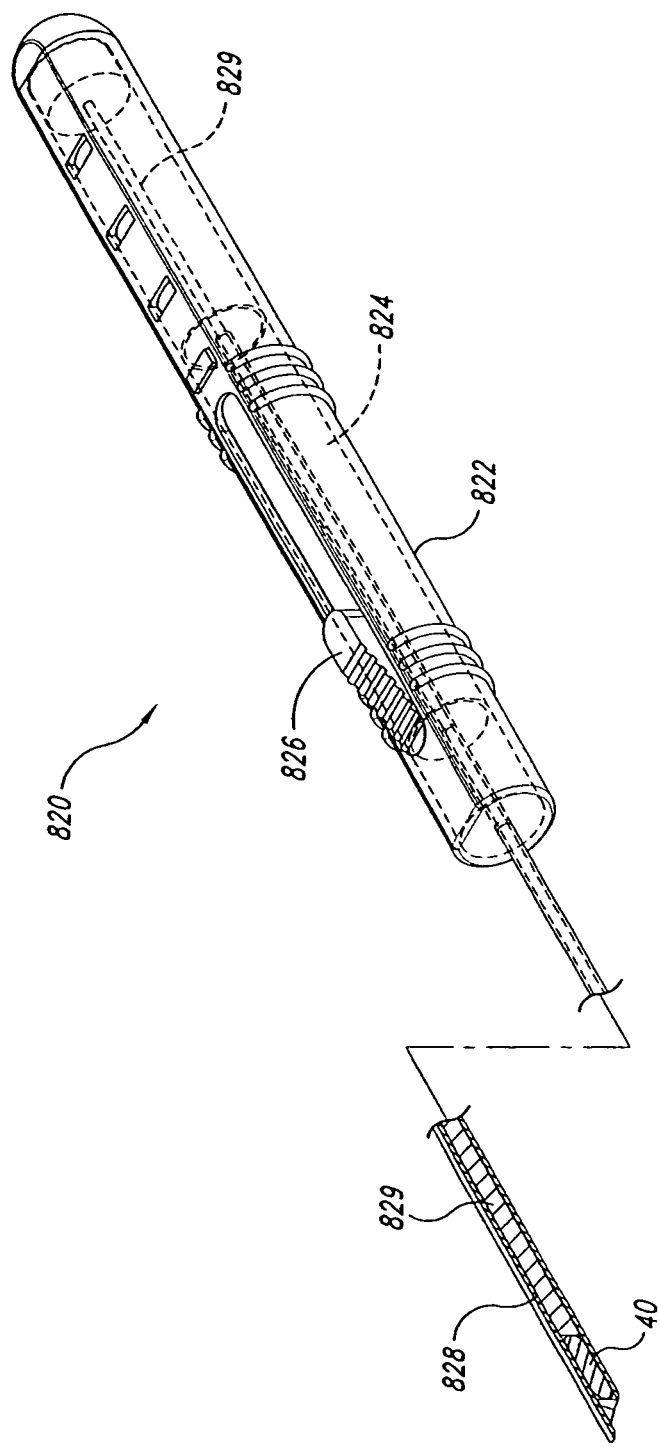
FIG. 9 is an isometric view with a cross-sectional portion illustrating a delivery device in accordance with another embodiment of the invention.

FIG. 9 is an isometric view of a delivery device 820 in accordance with another embodiment of the invention. The delivery device 820 can be a needle or other type of introducer for percutaneously implanting the marker 40 into the lung of the patient trans-thoracically. The delivery device 820 includes a handle 822, a slider 824 received in the handle 822, and an actuator 826 attached to the slider 824. The delivery device 820 further includes a cannula 828 attached to the slider 824 and a stylet 829 fixedly attached to the handle 822. In operation, the cannula 828 and stylet 829 are percutaneously inserted into the patient. When the marker 40 is at a desired location relative to the target, the actuator 826 is drawn proximately to move the slider 824 proximally within the handle 822. This motion withdraws the cannula 828 over the stylet 829 to release the marker 40 in the patient. The delivery device 820 and several other embodiments of delivery devices for percutaneous implantation of the markers are described in U.S. Patent Application No. 60/590,521 and Ser. No. 10/334,699, both of which are incorporated herein by reference in their entirety.

Figure 10:
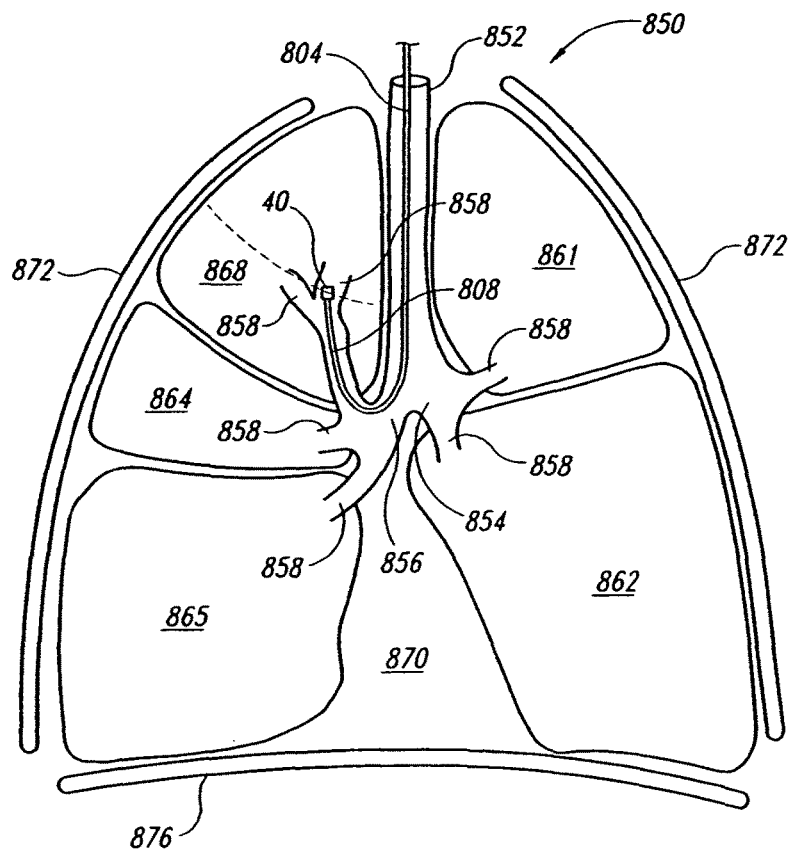
FIG. 10 is a schematic cross-sectional view of the operation of a delivery device in accordance with an embodiment of the invention.

FIG. 10 is a schematic cross-sectional view of a method for deploying a marker in accordance with an embodiment of a method of the invention. FIG. 10, more specifically, illustrates a portion of the respiratory system 850 of the patient. The respiratory system 850 resides within the thorax 870 and occupies a space defined by the chest 872 and the diaphragm 876. The respiratory system 850 further includes the trachea 852, the left mainstem bronchus 854, the right mainstem bronchus 856, and a plurality of bronchi 858 branching off of the mainstem bronchi and each other. For example, the bronchi 858 can include the primary bronchi (lobar bronchi), secondary bronchi (segmental bronchi) branching off of the primary bronchi, and tertiary bronchi (intersegmental bronchi) branching off of the secondary bronchi. The bronchi provide passageways to the lung lobes 861, 862, 863, 864, and 865.

One aspect of several embodiments of apparatus and methods in accordance with the invention is accurately guiding the delivery device 800 to a desired site relative to the target. In one embodiment, the distal section of the delivery device can be guided by localizing the marker 40 in real time before releasing the marker in a manner analogous to the localization of the markers 40a-c explained above. In other embodiments, the delivery device 800 can include a separate leadless marker similar to the marker 40 that is fixed to the body 804 and localized according to the processes explained above, or the delivery device 800 can include a radiopaque marker fixed to the body for fluoroscopic localization. In still another embodiment, the delivery device 800 can include a wired system having a plurality of sensors and/or transponders for electromagnetically locating the tip of the catheter. The wired markers are attached to the delivery device 800 and are in addition to the leadless marker 40 releasably carried at the distal section 808 of the elongated body 804. Suitable wired navigation systems are disclosed in the following U.S. patents and U.S. patent publications, which are incorporated by reference herein in their entirety: U.S. Pat. No. 6,833,814 B2; U.S. Pat. No. 6,711,429 B1; U.S. Pat. No. 6,615,155 B2; U.S. Pat. No. 6,574,498 B1; U.S. Pat. No. 6,558,333 B2; U.S. Pat. No. 6,188,355 B1; U.S. Pat. No. 6,226,543 B1, U.S. Pat. No. 6,593,884 B1; US 2004/0006268 A1; US 2002/0193686 A1; US 2003/0074011 A1; US 2003/0216639 A1; US 2001/0031985 A1; US 2003/0160721 A1; US 2002/0062203 A1; US 2002/0042571 A1; and US 2202/0005719 A1. In alternative embodiments, the delivery device 800 can be guided under fluoroscopic or optical (e.g., bronchoscope) procedures known in the art.

To deploy a marker in a lumen of the respiratory system, the distal portion 808 of the elongated body 804 is typically inserted through the mouth or nose of the patient and into the trachea 852. When the elongated body 804 is rigid, the distal section of the elongated body is typically positioned along the trachea 852 or another passageway of the lung generally proximate to the trachea 852. In the embodiment shown in FIG. 10, the elongated body 804 is flexible and can be guided and steered into any number of the bronchi to position the marker deeper within the lung. The distal section 808 of the elongated body 804 can be guided into such locations as described above using magnetic, optical, or fluoroscopic guidance systems. Additionally, the distal section 808 of the elongated body 804 can be steered using the steering mechanisms explained above or other suitable mechanisms for changing the direction of the distal section 808. When the marker 40 is at the desired location relative to the tumor, the marker 40 is released from the elongated body 804 and implanted in the particular passageway of the lung.

In an alternative embodiment, the distal section 808 of the elongated body 804 is passed through a lumen wall of one of the passageways to implant the marker 804 into the tissue of the lung or other tissue near the lung. In another alternative embodiment, a percutaneous implanter such as the delivery device 820 illustrated in FIG. 9 is passed through the thorax 870 to implant the marker into the tissue of the lung.

2. Markers

Figure 11A:
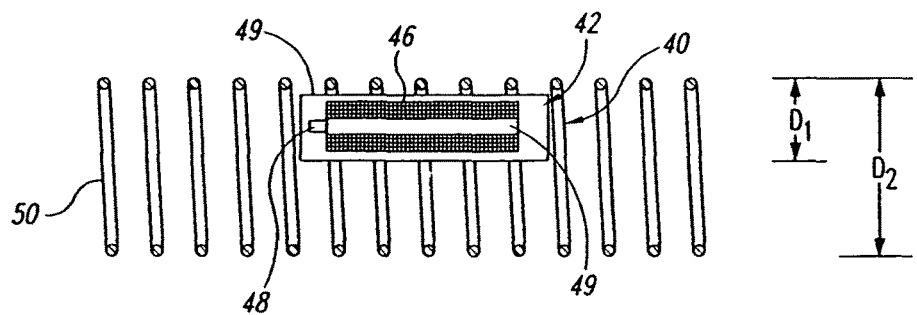
FIG. 11A is a cross-sectional view of a marker and an anchor in accordance with an embodiment of the invention.

FIG. 11A is a cross-sectional view illustrating an embodiment of one of the markers 40. In this embodiment, the marker 40 includes a transponder 42 including a core 44, a coil 46 around the core 44, and a capacitor 48 electrically coupled to the coil 46. The core 44 is typically composed of ferrite, and the coil 46 includes a plurality of windings of a wire around the core 44. The transponder 42 can be contained in a capsule 49 configured to be implanted into the patient. The capsule 49 is typically a biocompatible material. The transponder 42 has a small cross-sectional dimension in many applications. For example, the transponder 42 can have a cylindrical portion with a diameter from 0.5-3 mm and desirably from 1-2 mm. The transponder 42 is a resonating magnetic circuit that receives a wirelessly transmitted excitation energy and produces a wirelessly transmitted location signal in response to the excitation energy. The transponder 42 accordingly has a resonant frequency at which the excitation energy powers a transponder. Several specific details of different embodiments of localization systems 10 and markers 40 are described below with reference to FIGS. 11B-24.

The marker 40 shown in FIG. 11A also includes an anchor for attaching the marker 40 to a passageway in or adjacent to the lung 4 of the patient 6. The anchor 50 shown in FIG. 11A is a helical stent attached to the capsule 49. The anchor 50 moves radially with respect to the longitudinal axis of the marker between a retracted position and a deployed position. The anchor 50, for example, can have a first diameter $D_1$ in the retracted position to fit within a bronchoscope or a percutaneous trans-thoracic introducer. After being ejected from the introducer, the anchor 50 expands to a second diameter $D_2$ larger than the first diameter $D_1$, in the deployed position to engage the inner wall of a lumen (e.g., respiratory passageway). In operation, the anchor 50 presses radially outward against the inner wall of the lumen to hold the marker 40 in the passageway. The anchor 50 can also have other embodiments as set forth in the U.S. application Ser. No. 10/438,550, which is incorporated herein by reference, and the anchor 50 can be used with any of the markers described below with reference to FIGS. 12A-16.

Figure 11B:
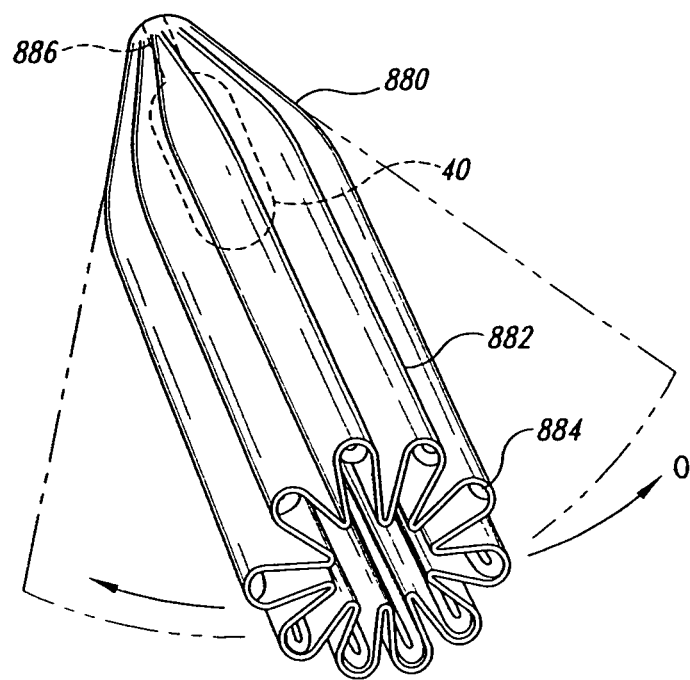
FIG. 11B is an isometric view of a marker and an anchor in accordance with another embodiment of the invention.

FIG. 11B illustrates the marker 40 with another embodiment of an anchor 880 for securing the marker 40 within a passageway in or near the lung 4 of the patient 6. The anchor 880 includes an umbrella-like cover 882 supported by a plurality of links 884 that move outwardly (arrow O) from a stored position shown in solid lines to a deployed position shown in broken lines. The marker 880 further includes a tether or attachment device 886 connecting the marker 40 to the anchor 880. In operation, the anchor 880 expands into the deployed position to hold the marker within the lumen as the marker is released from a catheter or bronchoscope.

Figure 11C:
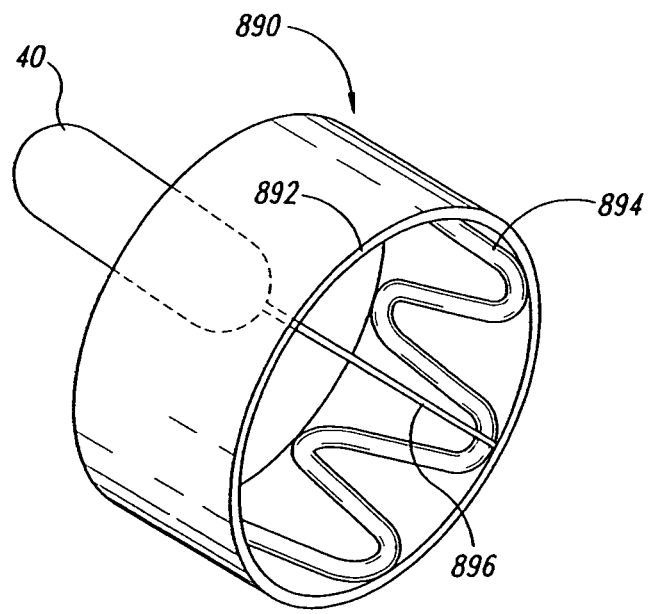
FIG. 11C is an isometric view of a marker and an anchor in accordance with another embodiment of the invention.

FIG. 11C illustrates the marker 40 with an anchor 890 in accordance with another embodiment of the invention. In this embodiment, the anchor 890 includes a cylindrical section 892 and a resilient member 894 attached to the cylindrical section 892 for urging the cylindrical 892 radially outward. The anchor 890 further includes a tether 896 attaching the marker 40 the anchor 890. The anchors 880 and 890 and other suitable anchors for deployment of the markers 40 are disclosed in the following U.S. patents and U.S. patent application publication, which are herein incorporated by reference in their entirety: U.S. Pat. No. 6,258,100 B1; U.S. Pat. No. 6,592,594 B2; and US 2003/0212412 A1.

Figure 12A:
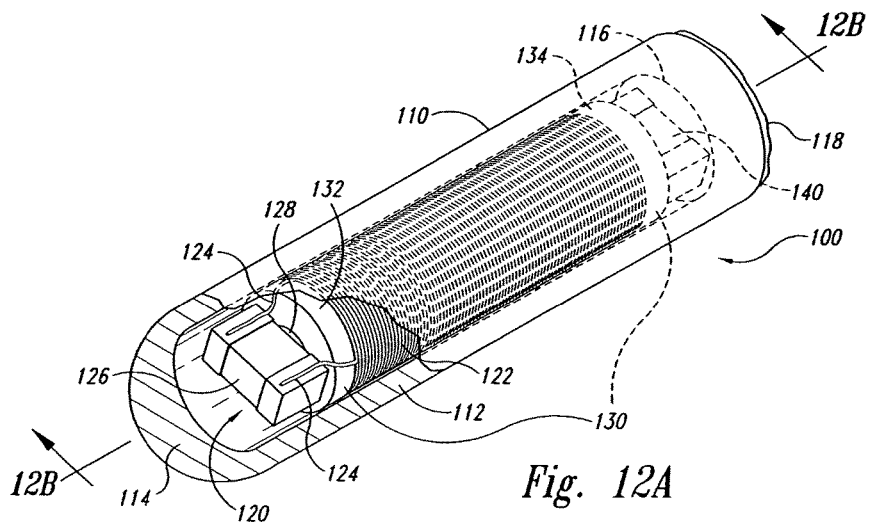
FIG. 12A is an isometric view of a marker for use with a localization system in accordance with an embodiment of the invention.

FIG. 12A is an isometric view of a marker 100 for use with the localization system 10 (FIGS. 1-7). The embodiment of the marker 100 shown in FIG. 12A includes a casing 110 and a magnetic transponder 120 (e.g., a resonating circuit) in the casing 110. The casing 110 is a barrier configured to be implanted in the patient, or encased within the body of an instrument. The casing 110 can alternatively be configured to be adhered externally to the skin of the patient. The casing 110 can be a generally cylindrical capsule that is sized to fit within the bore of a small introducer, such as bronchoscope or percutaneous trans-thoracic implanter, but the casing 110 can have other configurations and be larger or smaller. The casing 110, for example, can have barbs or other features to anchor the casing 110 in soft tissue or an adhesive for attaching the casing 110 externally to the skin of a patient. Suitable anchoring mechanisms for securing the marker 100 to a patient are disclosed in International Publication No. WO 02/39917 A1, which designates the United States and is incorporated herein by reference. In one embodiment, the casing 110 includes (a) a capsule or shell 112 having a closed end 114 and an open end 116, and (b) a sealant 118 in the open end 116 of the shell 112. The casing 110 and the sealant 118 can be made from plastics, ceramics, glass or other suitable biocompatible materials.

The magnetic transponder 120 can include a resonating circuit that wirelessly transmits a location signal in response to a wirelessly transmitted excitation field as described above. In this embodiment, the magnetic transponder 120 comprises a coil 122 defined by a plurality of windings of a conductor 124. Many embodiments of the magnetic transponder 120 also include a capacitor 126 coupled to the coil 122. The coil 122 resonates at a selected resonant frequency. The coil 122 can resonate at a resonant frequency solely using the parasitic capacitance of the windings without having a capacitor, or the resonant frequency can be produced using the combination of the coil 122 and the capacitor 126. The coil 122 accordingly generates an alternating magnetic field at the selected resonant frequency in response to the excitation energy either by itself or in combination with the capacitor 126. The conductor 124 of the illustrated embodiment can be hot air or alcohol bonded wire having a gauge of approximately 45-52. The coil 122 can have 800-1000 turns, and the windings are preferably wound in a tightly layered coil. The magnetic transponder 120 can further include a core 128 composed of a material having a suitable magnetic permeability. For example, the core 128 can be a ferromagnetic element composed of ferrite or another material. The magnetic transponder 120 can be secured to the casing 110 by an adhesive 129.

The marker 100 also includes an imaging element that enhances the radiographic image of the marker to make the marker more discernible in radiographic images. The imaging element also has a radiographic profile in a radiographic image such that the marker has a radiographic centroid at least approximately coincident with the magnetic centroid of the magnetic transponder 120. As explained in more detail below, the radiographic and magnetic centroids do not need to be exactly coincident with each other, but rather can be within an acceptable range.

Figure 12B:
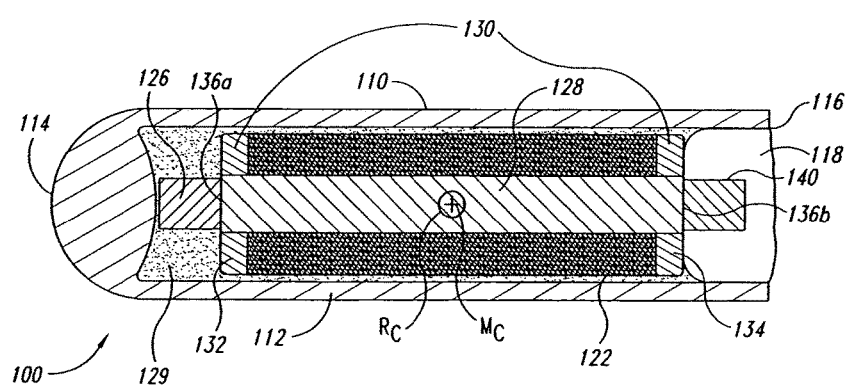
FIG. 12B is a cross-sectional view of the marker of FIG. 12A taken along line 12B-12B.

FIG. 12B is a cross-sectional view of the marker 100 along line 12B-12B of FIG. 12A that illustrates an imaging element 130 in accordance with an embodiment of the invention. The imaging element 130 illustrated in FIGS. 12A-B includes a first contrast element 132 and second contrast element 134. The first and second contrast elements 132 and 134 are generally configured with respect to the magnetic transponder 120 so that the marker 100 has a radiographic centroid $R_v$ that is at least substantially coincident with the magnetic centroid $M_c$ of the magnetic transponder 120. For example, when the imaging element 130 includes two contrast elements, the contrast elements can be arranged symmetrically with respect to the magnetic transponder 120 and/or each other. The contrast elements can also be radiographically distinct from the magnetic transponder 120. In such an embodiment, the symmetrical arrangement of distinct contrast elements enhances the ability to accurately determine the radiographic centroid of the marker 100 in a radiographic image.

The first and second contrast elements 132 and 134 illustrated in FIGS. 12A-B are continuous rings positioned at opposing ends of the core 128. The first contrast element 132 can be at or around a first end 136a of the core 128, and the second contrast element 134 can be at or around a second end 136b of the core 128. The continuous rings shown in FIGS. 12A-B have substantially the same diameter and thickness. The first and second contrast elements 132 and 134, however, can have other configurations and/or be in other locations relative to the core 128 in other embodiments. For example, the first and second contrast elements 132 and 134 can be rings with different diameters and/or thicknesses.

The radiographic centroid of the image produced by the imaging element 130 does not need to be absolutely coincident with the magnetic centroid $M_c$, but rather the radiographic centroid and the magnetic centroid should be within an acceptable range. For example, the radiographic centroid $R_c$ can be considered to be at least approximately coincident with the magnetic centroid $M_c$ when the offset between the centroids is less than approximately 5 mm. In more stringent applications, the magnetic centroid $M_c$ and the radiographic centroid $R_c$ are considered to be at least substantially coincident with each other when the offset between the centroids is 2 mm, or less than 1 mm. In other applications, the magnetic centroid $M_c$ is at least approximately coincident with the radiographic centroid $R_c$ when the centroids are spaced apart by a distance not greater than half the length of the magnetic transponder 120 and/or the marker 100.

The imaging element 130 can be made from a material and configured appropriately to absorb a high fraction of incident photons of a radiation beam used for producing the radiographic image. For example, when the imaging radiation has high acceleration voltages in the megavoltage range, the imaging element 130 is made from, at least in part, high density materials with sufficient thickness and cross-sectional area to absorb enough of the photon fluence incident on the imaging element to be visible in the resulting radiograph. Many high energy beams used for therapy have acceleration voltages of 6 MV-25 MV, and these beams are often used to produce radiographic images in the 5 MV-10 MV range, or more specifically in the 6 MV-8 MV range. As such, the imaging element 130 can be made from a material that is sufficiently absorbent of incident photon fluence to be visible in an image produced using a beam with an acceleration voltage of 5 MV-10 MV, or more specifically an acceleration voltage of 6 MV-8 MV.

Several specific embodiments of imaging elements 130 can be made from gold, tungsten, platinum and/or other high density metals. In these embodiments the imaging element 130 can be composed of materials having a density of 19.25 g/cm3 (density of tungsten) and/or a density of approximately 21.4 g/cm3 (density of platinum). Many embodiments of the imaging element 130 accordingly have a density not less than 19 g/cm3. In other embodiments, however, the material(s) of the imaging element 130 can have a substantially lower density. For example, imaging elements with lower density materials are suitable for applications that use lower energy radiation to produce radiographic images. Moreover, the first and second contrast elements 132 and 134 can be composed of different materials such that the first contrast element 132 can be made from a first material and the second contrast element 134 can be made from a second material.

Referring to FIG. 12B, the marker 100 can further include a module 140 at an opposite end of the core 128 from the capacitor 126. In the embodiment of the marker 100 shown in FIG. 12B, the module 140 is configured to be symmetrical with respect to the capacitor 126 to enhance the symmetry of the radiographic image. As with the first and second contrast elements 132 and 134, the module 140 and the capacitor 126 are arranged such that the magnetic centroid of the marker is at least approximately coincident with the radiographic centroid of the marker 100. The module 140 can be another capacitor that is identical to the capacitor 126, or the module 140 can be an electrically inactive element. Suitable electrically inactive modules include ceramic blocks shaped like the capacitor 126 and located with respect to the coil 122, the core 128 and the imaging element 130 to be symmetrical with each other. In still other embodiments the module 140 can be a different type of electrically active element electrically coupled to the magnetic transponder 120.

One specific process of using the marker involves imaging the marker using a first modality and then tracking the target of the patient and/or the marker using a second modality. For example, the location of the marker relative to the target can be determined by imaging the marker and the target using radiation. The marker and/or the target can then be localized and tracked using the magnetic field generated by the marker in response to an excitation energy.

Figure 12C:
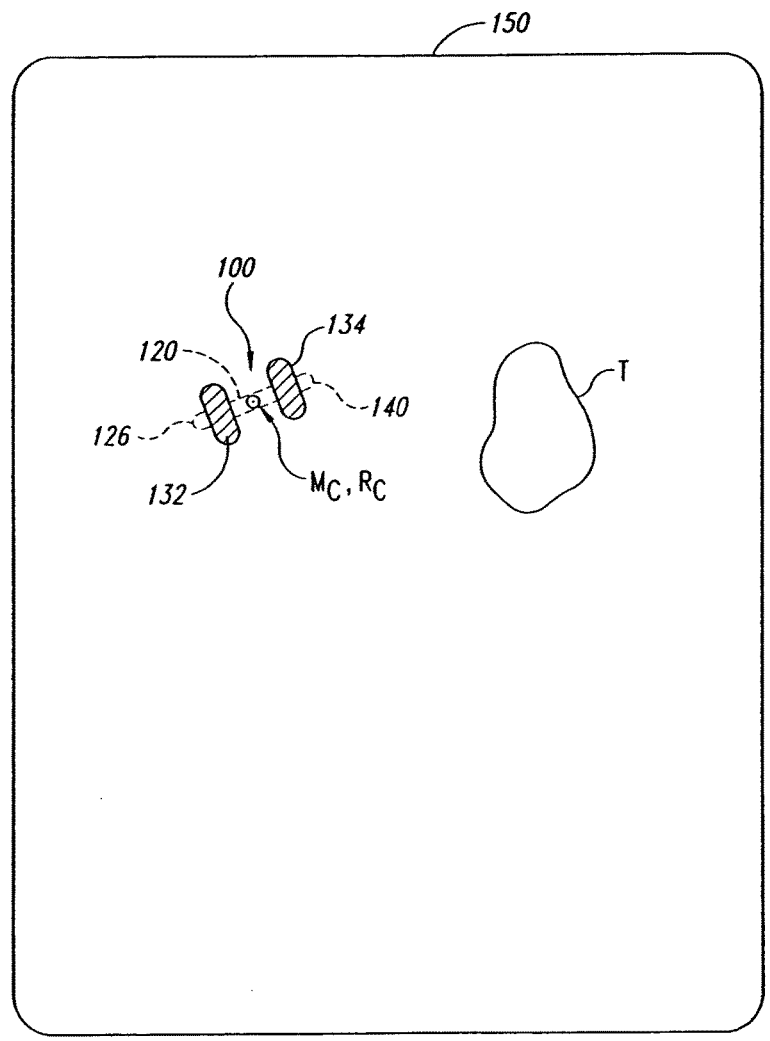
FIG. 12C is an illustration of a radiographic image of the marker of FIGS. 12A-B.

The marker 100 shown in FIGS. 12A-B is expected to provide an enhanced radiographic image compared to conventional magnetic markers for more accurately determining the relative position between the marker and the target of a patient. FIG. 12C, for example, illustrates a radiographic image 150 of the marker 100 and a target T of the patient. The first and second contrast elements 132 and 134 are expected to be more distinct in the radiographic image 150 because they can be composed of higher density materials than the components of the magnetic transponder 120. The first and second contrast elements 132 and 134 can accordingly appear as bulbous ends of a dumbbell shape in applications in which the components of the magnetic transponder 120 are visible in the image. In certain megavolt applications, the components of the magnetic transponder 120 may not appear at all on the radiographic image 150 such that the first and second contrast elements 132 and 134 will appear as distinct regions that are separate from each other. In either embodiment, the first and second contrast elements 132 and 134 provide a reference frame in which the radiographic centroid $R_c$ of the marker 100 can be located in the image 150. Moreover, because the imaging element 130 is configured so that the radiographic centroid $R_c$ is at least approximately coincident with the magnetic centroid $M_c$, the relative offset or position between the target T and the magnetic centroid $M_c$ can be accurately determined using the marker 100. The embodiment of the marker 100 illustrated in FIGS. 12A-C, therefore, is expected to mitigate errors caused by incorrectly estimating the radiographic and magnetic centroids of markers in radiographic images.

Figure 13A:
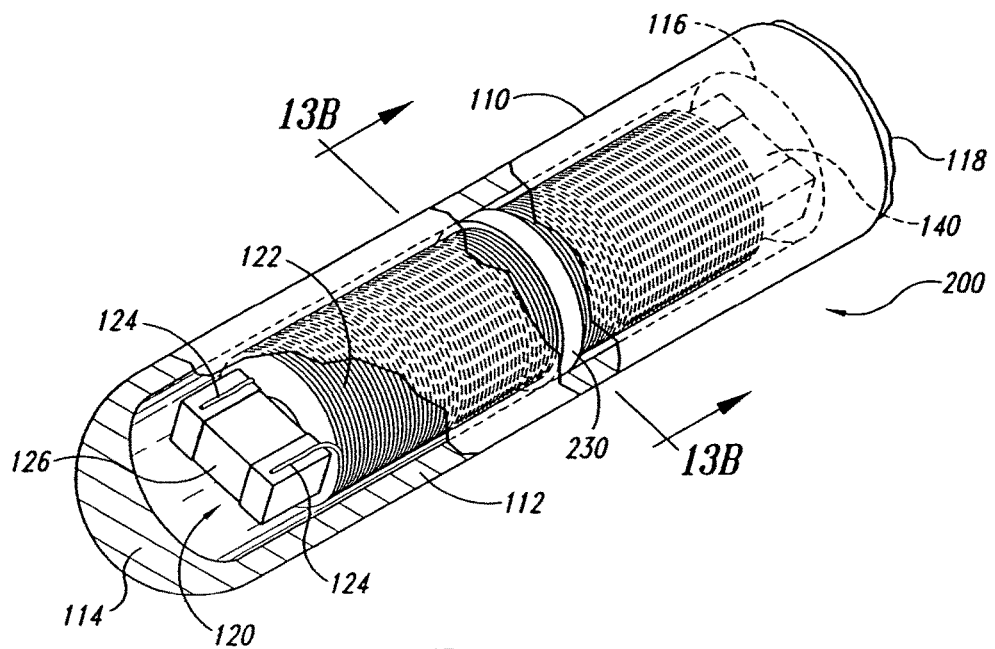
FIG. 13A is an isometric view of a marker for use with a localization system in accordance with another embodiment of the invention.
Figure 13B:
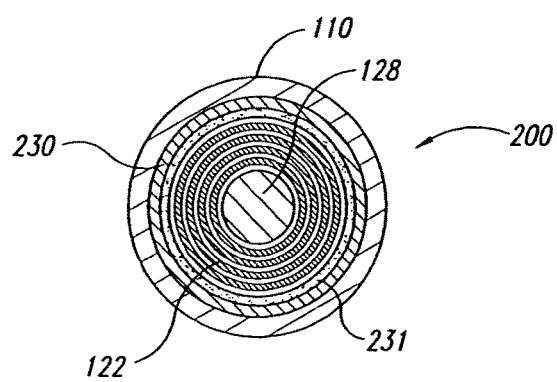
FIG. 13B is a cross-sectional view of the marker of FIG. 13A taken along line 13B-13B.

FIG. 13A is an isometric view of a marker 200 with a cut-away portion to illustrate internal components, and FIG. 13B is a cross-sectional view of the marker 200 taken along line 13B-13B of FIG. 13A. The marker 200 is similar to the marker 100 shown above in FIG. 12A, and thus like reference numbers refer to like components. The marker 200 differs from the marker 100 in that the marker 200 includes an imaging element 230 defined by a single contrast element. The imaging element 230 is generally configured relative to the magnetic transponder 120 so that the radiographic centroid of the marker 200 is at least approximately coincident with the magnetic centroid of the magnetic transponder 120. The imaging element 230, more specifically, is a ring extending around the coil 122 at a medial region of the magnetic transponder 120. The imaging element 230 can be composed of the same materials described above with respect to the imaging element 130 in FIGS. 12A-B. The imaging element 230 can have an inner diameter that is approximately equal to the outer diameter of the coil 122, and an outer diameter within the casing 110. As shown in FIG. 13B, however, a spacer 231 can be between the inner diameter of the imaging element 230 and the outer diameter of the coil 122.

The marker 200 is expected to operate in a manner similar to the marker 100 described above. The marker 200, however, does not have two separate contrast elements that provide two distinct, separate points in a radiographic image. The imaging element 230 is still highly useful in that it identifies the radiographic centroid of the marker 200 in a radiographic image, and it can be configured so that the radiographic centroid of the marker 200 is at least approximately coincident with the magnetic centroid of the magnetic transponder 120.

Figure 14A:
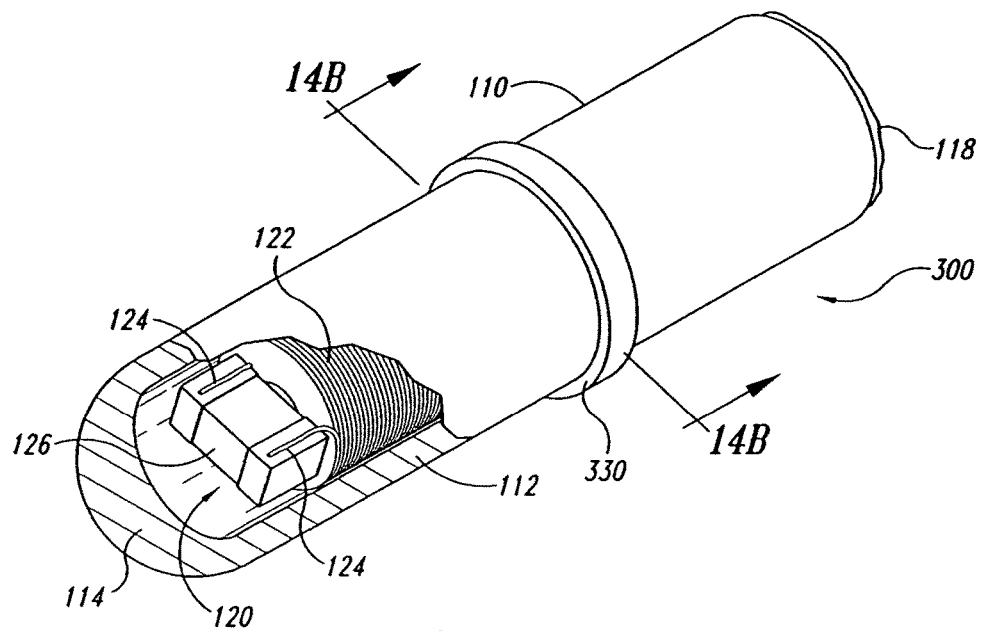
FIG. 14A is an isometric view of a marker for use with a localization system in accordance with another embodiment of the invention.
Figure 14B:
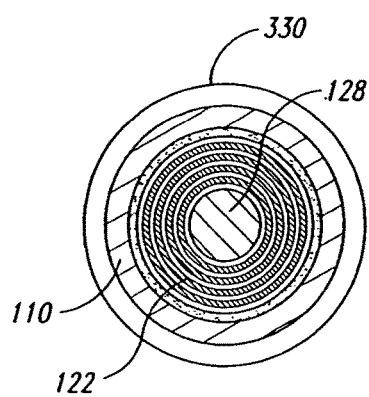
FIG. 14B is a cross-sectional view of the marker of FIG. 14A taken along line 14B-14B.

FIG. 14A is an isometric view of a marker 300 having a cut-away portion, and FIG. 14B is a cross-sectional view of the marker 300 taken along line 14B-14B of FIG. 14A. The marker 300 is substantially similar to the marker 200 shown in FIGS. 13A-B, and thus like reference numbers refer to like components in FIGS. 12A-14B. The imaging element 330 can be a high density ring configured relative to the magnetic transponder 120 so that the radiographic centroid of the marker 300 is at least approximately coincident with the magnetic centroid of the magnetic transponder 120. The marker 300, more specifically, includes an imaging element 330 around the casing 110. The marker 300 is expected to operate in much the same manner as the marker 200 shown in FIGS. 13A-B.

Figure 15:
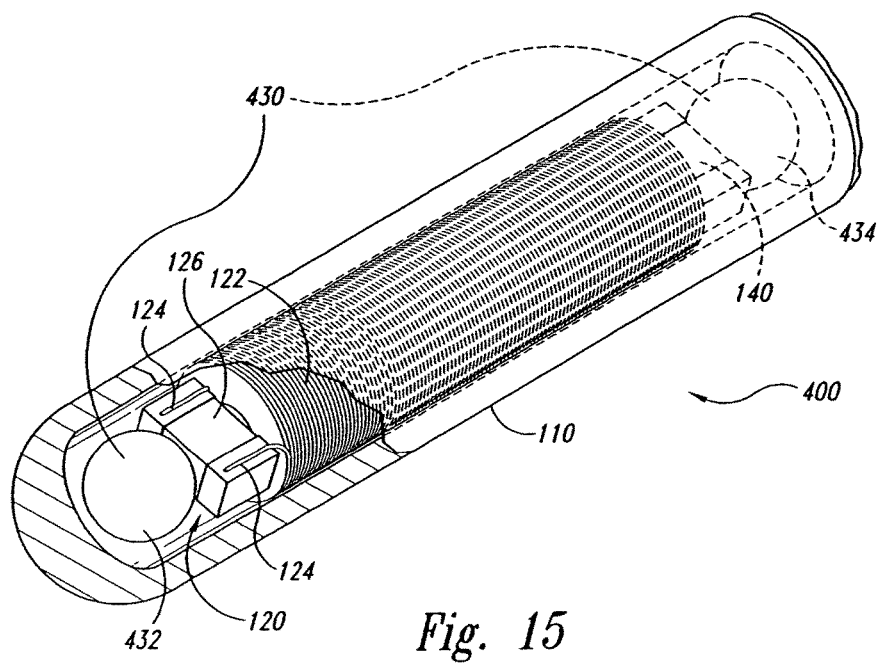
FIG. 15 is an isometric view of a marker for use with a localization system in accordance with another embodiment of the invention.

FIG. 15 is an isometric view with a cut-away portion illustrating a marker 400 in accordance with another embodiment of the invention. The marker 400 is similar to the marker 100 shown in FIGS. 12A-C, and thus like reference numbers refer to like components in these Figures. The marker 400 has an imaging element 430 including a first contrast element 432 at one end of the magnetic transponder 120 and a second contrast element 434 at another end of the magnetic transponder 120. The first and second contrast elements 432 and 434 are spheres composed of suitable high density materials. The contrast elements 432 and 434, for example, can be composed of gold, tungsten, platinum or other suitable high-density materials for use in radiographic imaging. The marker 400 is expected to operate in a manner similar to the marker 100, as described above.

Figure 16:
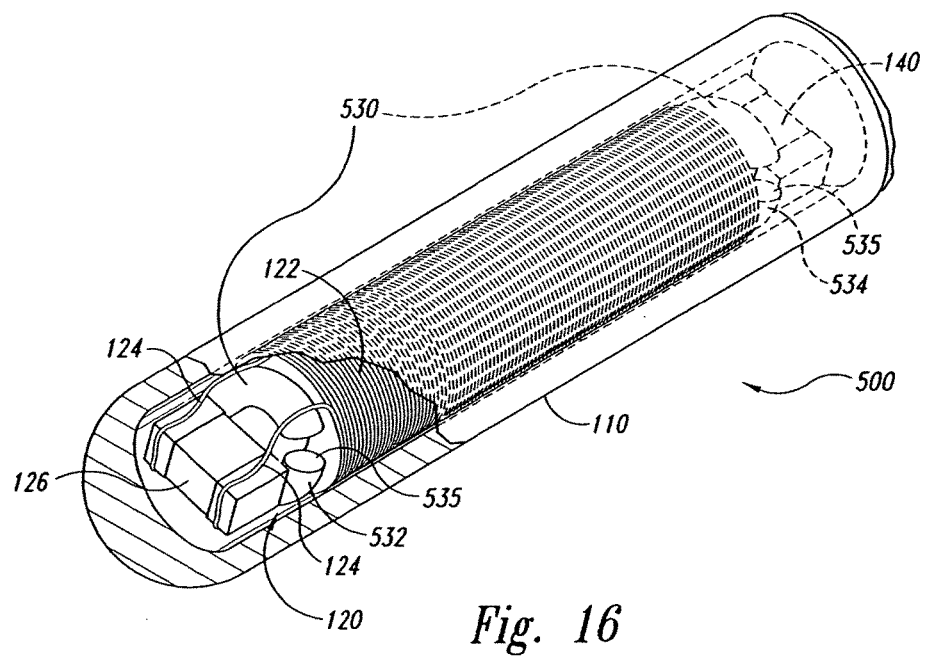
FIG. 16 is an isometric view of a marker for use with a localization system in accordance with yet another embodiment of the invention.

FIG. 16 is an isometric view with a cut-away portion of a marker 500 in accordance with yet another embodiment of the invention. The marker 500 is substantially similar to the markers 100 and 400 shown in FIGS. 12A and 15, and thus like reference numbers refer to like components in these Figures. The marker 500 includes an imaging element 530 including a first contrast element 532 and a second contrast element 534. The first and second contrast elements 532 and 534 can be positioned proximate to opposing ends of the magnetic transponder 120. The first and second contrast elements 532 and 534 can be discontinuous rings having a gap 535 to mitigate eddy currents. The contrast elements 532 and 534 can be composed of the same materials as described above with respect to the contrast elements of other imaging elements in accordance with other embodiments of the invention.

Additional embodiments of markers in accordance with the invention can include imaging elements incorporated into or otherwise integrated with the casing 110, the core 128 (FIG. 12B) of the magnetic transponder 120, and/or the adhesive 129 (FIG. 12B) in the casing. For example, particles of a high density material can be mixed with ferrite and extruded to form the core 128. Alternative embodiments can mix particles of a high density material with glass or another material to form the casing 110, or coat the casing 110 with a high-density material. In still other embodiments, a high density material can be mixed with the adhesive 129 and injected into the casing 110. Any of these embodiments can incorporate the high density material into a combination of the casing 110, the core 128 and/or the adhesive 129. Suitable high density materials can include tungsten, gold and/or platinum as described above.

The markers described above with reference to FIGS. 12A-16 can be used for the markers 40 in the localization system 10 (FIGS. 1-7). The localization system 10 can have several markers with the same type of imaging elements, or markers with different imaging elements can be used with the same instrument. Several additional details of these markers and other embodiments of markers are described in U.S. application Ser. Nos. 10/334,698 and 10/746,888, which are incorporated herein by reference. For example, the markers may not have any imaging elements for applications with lower energy radiation, or the markers may have reduced volumes of ferrite and metals to mitigate issues with MRI imaging as set forth in U.S. application Ser. No. 10/334,698.

3. Localization Systems

Figure 17:
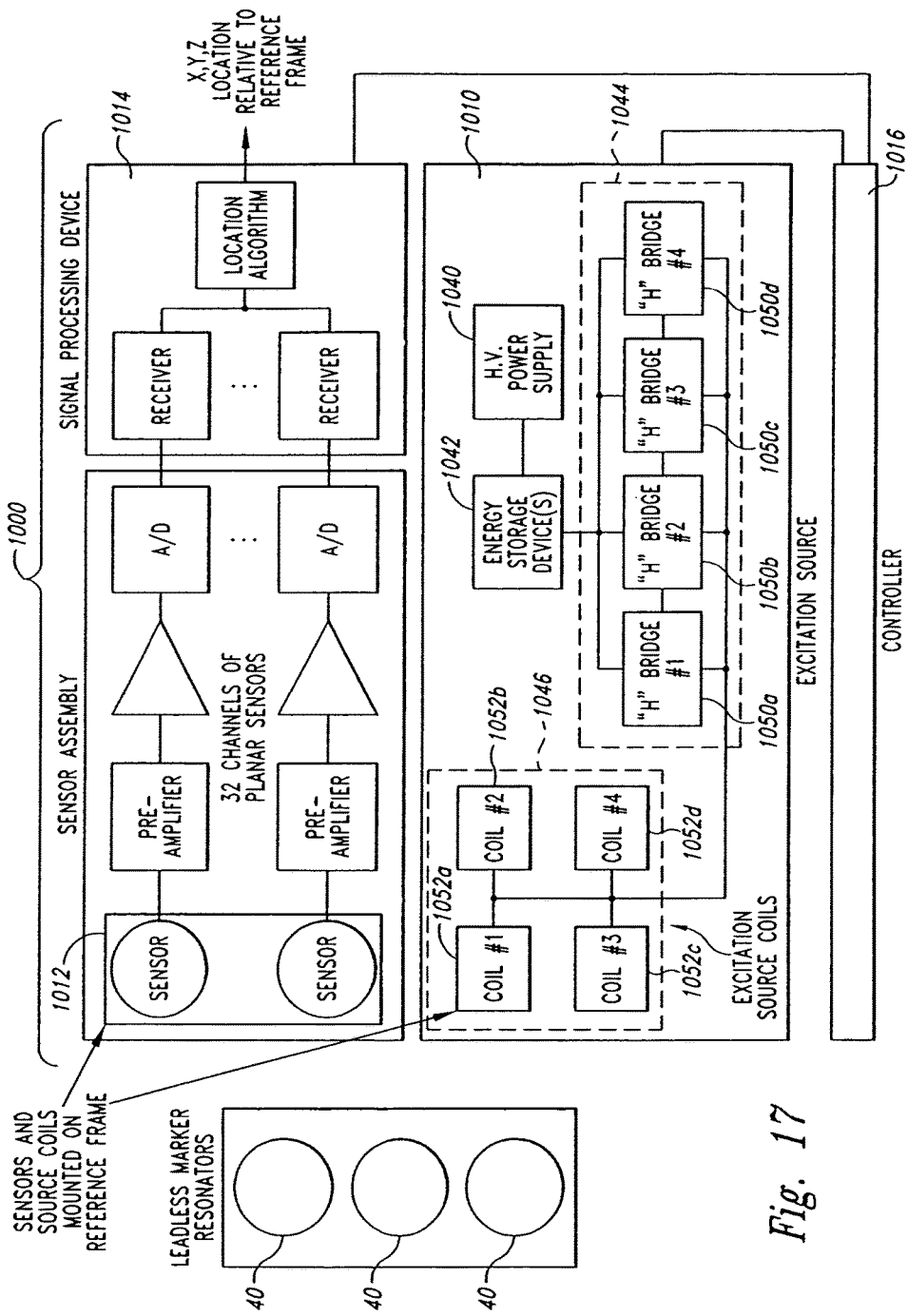
FIG. 17 is a schematic block diagram of a localization system for use in tracking a target in accordance with an embodiment of the invention.

FIG. 17 is a schematic block diagram of a localization system 1000 for determining the absolute location of the markers 40 (shown schematically) relative to a reference frame. The localization system 1000 includes an excitation source 1010, a sensor assembly 1012, a signal processor 1014 operatively coupled to the sensor assembly 1012, and a controller 1016 operatively coupled to the excitation source 1010 and the signal processor 1014. The excitation source 1010 is one embodiment of the excitation source 60 described above with reference to FIG. 3; the sensor assembly 1012 is one embodiment of the sensor assembly 70 described above with reference to FIG. 3; and the controller 1016 is one embodiment of the controller 80 described above with reference to FIG. 3.

The excitation source 1010 is adjustable to generate a magnetic field having a waveform with energy at selected frequencies to match the resonant frequencies of the markers 40. The magnetic field generated by the excitation source 1010 energizes the markers at their respective frequencies. After the markers 40 have been energized, the excitation source 1010 is momentarily switched to an "off" position so that the pulsed magnetic excitation field is terminated while the markers wirelessly transmit the location signals. This allows the sensor assembly 1012 to sense the location signals from the markers 40 without measurable interference from the significantly more powerful magnetic field from the excitation source 1010. The excitation source 1010 accordingly allows the sensor assembly 1012 to measure the location signals from the markers 40 at a sufficient signal-to-noise ratio so that the signal processor 1014 or the controller 1016 can accurately calculate the absolute location of the markers 40 relative to a reference frame.

a. Excitation Sources

Referring still to FIG. 17, the excitation source 1010 includes a high voltage power supply 1040, an energy storage device 1042 coupled to the power supply 1040, and a switching network 1044 coupled to the energy storage device 1042. The excitation source 1010 also includes a coil assembly 1046 coupled to the switching network 1044. In one embodiment, the power supply 1040 is a 500 volt power supply, although other power supplies with higher or lower voltages can be used. The energy storage device 1042 in one embodiment is a high voltage capacitor that can be charged and maintained at a relatively constant charge by the power supply 1040. The energy storage device 1042 alternately provides energy to and receives energy from the coils in the coil assembly 1046.

The energy storage device 1042 is capable of storing adequate energy to reduce voltage drop in the energy storage device while having a low series resistance to reduce power losses. The energy storage device 1042 also has a low series inductance to more effectively drive the coil assembly 1046. Suitable capacitors for the energy storage device 1042 include aluminum electrolytic capacitors used in flash energy applications. Alternative energy storage devices can also include NiCd and lead acid batteries, as well as alternative capacitor types, such as tantalum, film, or the like.

The switching network 1044 includes individual H-bridge switches 1050 (identified individually by reference numbers 1050a-d), and the coil assembly 1046 includes individual source coils 1052 (identified individually by reference numbers 1052a-d). Each H-bridge switch 1050 controls the energy flow between the energy storage device 1042 and one of the source coils 1052. For example, H-bridge switch #1 1050a independently controls the flow of the energy to/from source coil #1 1052a, H-bridge switch #2 1050b independently controls the flow of the energy to/from source coil #2 1052b, H-bridge switch #3 1050c independently controls the flow of the energy to/from source coil #3 1052c, and H-bridge switch #4 1050d independently controls the flow of the energy to/from source coil #4 1052d. The switching network 1044 accordingly controls the phase of the magnetic field generated by each of the source coils 1052a-d independently. The H-bridges 1050 can be configured so that the electrical signals for all the source coils 1052 are in phase, or the H-bridge switches 1050 can be configured so that one or more of the source coils 1052 are 180° out of phase. Furthermore, the H-bridge switches 1050 can be configured so that the electrical signals for one or more of the source coils 1052 are between 0 and 180° out of phase to simultaneously provide magnetic fields with different phases.

The source coils 1052 can be arranged in a coplanar array that is fixed relative to the reference frame. Each source coil 1052 can be a square, planar winding arranged to form a flat, substantially rectilinear coil. The source coils 1052 can have other shapes and other configurations in different embodiments. In one embodiment, the source coils 1052 are individual conductive lines formed in a stratum of a printed circuit board, or windings of a wire in a foam frame. Alternatively, the source coils 1052 can be formed in different substrates or arranged so that two or more of the source coils are not planar with each other. Additionally, alternate embodiments of the invention may have fewer or more source coils than illustrated in FIG. 17.

The selected magnetic fields from the source coils 1052 combine to form an adjustable excitation field that can have different three-dimensional shapes to excite the markers 40 at any spatial orientation within an excitation volume. When the planar array of the source coils 1052 is generally horizontal, the excitation volume is positioned above an area approximately corresponding to the central region of the coil assembly 1046. The excitation volume is the three-dimensional space adjacent to the coil assembly 1046 in which the strength of the magnetic field is sufficient to adequately energize the markers 40.

Figure 18:
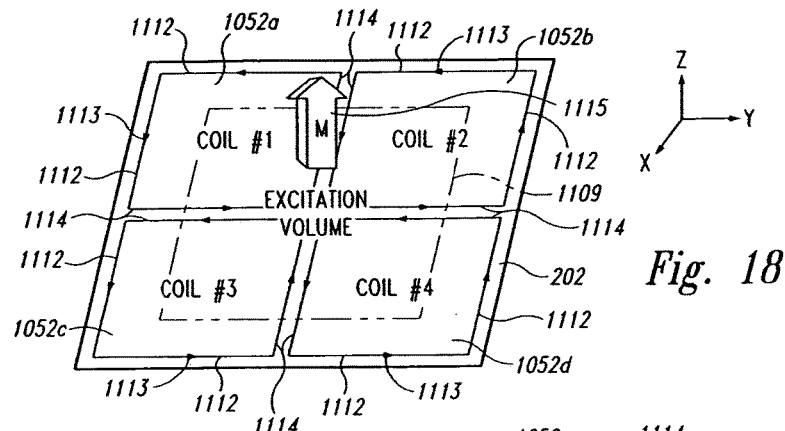
FIG. 18 is a schematic view of an array of coplanar source coils carrying electrical signals in a first combination of phases to generate a first excitation field.
Figure 19:
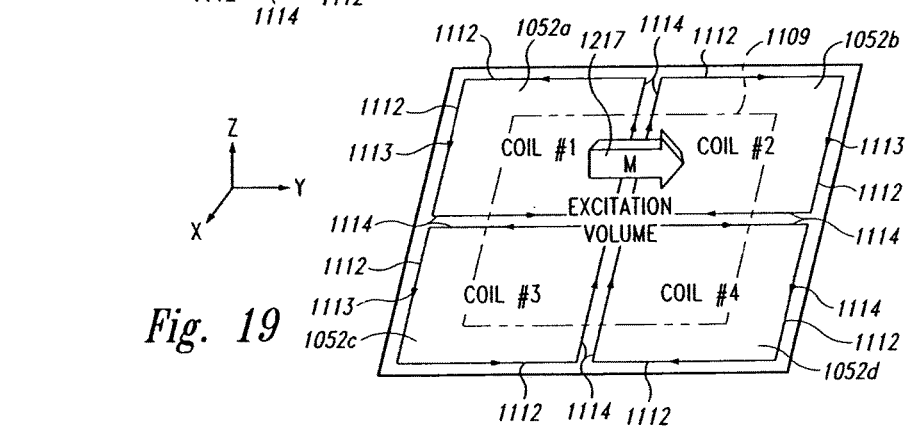
FIG. 19 is a schematic view of an array of coplanar source coils carrying electrical signals in a second combination of phases to generate a second excitation field.
Figure 20:
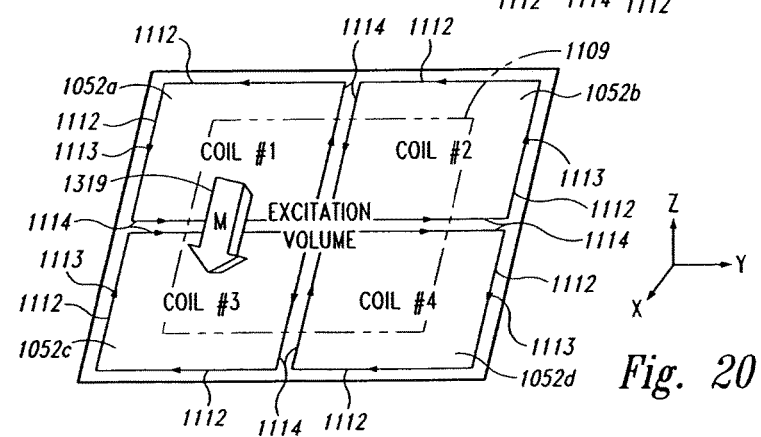
FIG. 20 is a schematic view of an array of coplanar source coils carrying electrical signals in a third combination of phases to generate a third excitation field.

FIGS. 18-20 are schematic views of a planar array of the source coils 1052 with the alternating electrical signals provided to the source coils in different combinations of phases to generate excitation fields about different axes relative to the illustrated XYZ coordinate system. Each source coil 1052 has two outer sides 1112 and two inner sides 1114. Each inner side 1114 of one source coil 1052 is immediately adjacent to an inner side 1114 of another source coil 1052, but the outer sides 1112 of all the source coils 1052 are not adjacent to any other source coil 1052.

In the embodiment of FIG. 18, all the source coils 1052a-d simultaneously receive an alternating electrical signals in the same phase. As a result, the electrical current flows in the same direction through all the source coils 1052a-d such that a direction 1113 of the current flowing along the inner sides 1114 of one source coil (e.g., source coil 1052a) is opposite to the direction 1113 of the current flowing along the inner sides 1114 of the two adjacent source coils (e.g., source coils 1052c and 1052d). The magnetic fields generated along the inner sides 1114 accordingly cancel each other out so that the magnetic field is effectively generated from the current flowing along the outer sides 1112 of the source coils. The resulting excitation field formed by the combination of the magnetic fields from the source coils 1052a-d shown in FIG. 18 has a magnetic moment 1115 generally in the Z direction within an excitation volume 1109. This excitation field energizes markers parallel to the Z-axis or markers positioned with an angular component along the Z-axis (i.e., not orthogonal to the Z-axis).

FIG. 19 is a schematic view of the source coils 1052a-d with the alternating electrical signals provided in a second combination of phases to generate a second excitation field with a different spatial orientation. In this embodiment, source coils 1052a and 1052c are in phase with each other, and source coils 1052b and 1052d are in phase with each other. However, source coils 1052a and 1052c are 180 degrees out of phase with source coils 1052*b* and 1052*d*. The magnetic fields from the source coils 1052*a-d* combine to generate an excitation field having a magnetic moment 1217 generally in the Y direction within the excitation volume 1109. Accordingly, this excitation field energizes markers parallel to the Y-axis or markers positioned with an angular component along the Y-axis.

FIG. 20 is a schematic view of the source coils 1052*a-d* with the alternating electrical signals provided in a third combination of phases to generate a third excitation field with a different spatial orientation. In this embodiment, source coils 1052*a* and 1052*b* are in phase with each other, and source coils 1052*c* and 1052*d* are in phase with each other. However, source coils 1052*a* and 1052*b* are 180 degrees out of phase with source coils 1052*c* and 1052*d*. The magnetic fields from the source coils 1052*a-d* combine to generate an excitation field having a magnetic moment 1319 in the excitation volume 1109 generally in the direction of the X-axis. Accordingly, this excitation field energizes markers parallel to the X-axis or markers positioned with an angular component along the X-axis.

Figure 21:
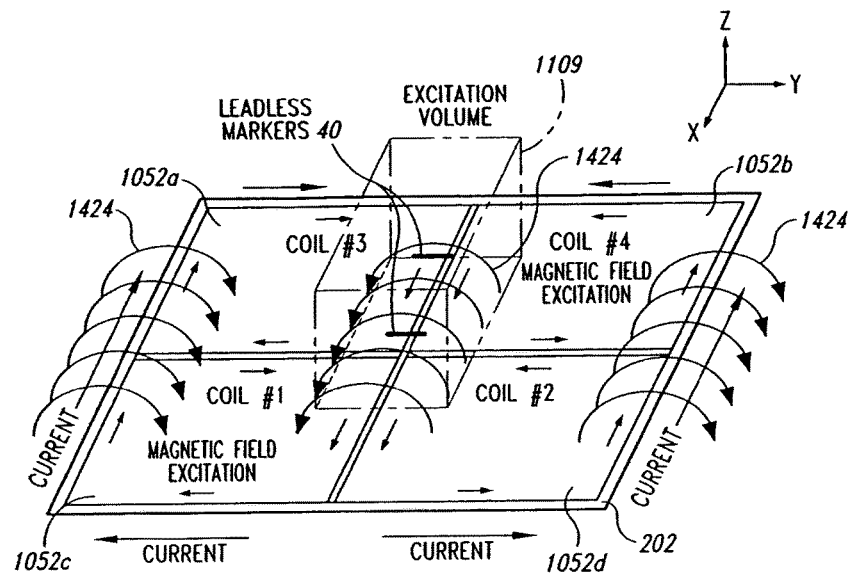
FIG. 21 is a schematic view of an array of coplanar source coils illustrating a magnetic excitation field for energizing markers in a first spatial orientation.

FIG. 21 is a schematic view of the source coils 1052*a-d* illustrating the current flow to generate an excitation field 1424 for energizing markers 40 with longitudinal axes parallel to the Y-axis. The switching network 1044 (FIG. 17) is configured so that the phases of the alternating electrical signals provided to the source coils 1052*a-d* are similar to the configuration of FIG. 18. This generates the excitation field 1424 with a magnetic moment in the Y direction to energize the markers 40.

Figure 22:
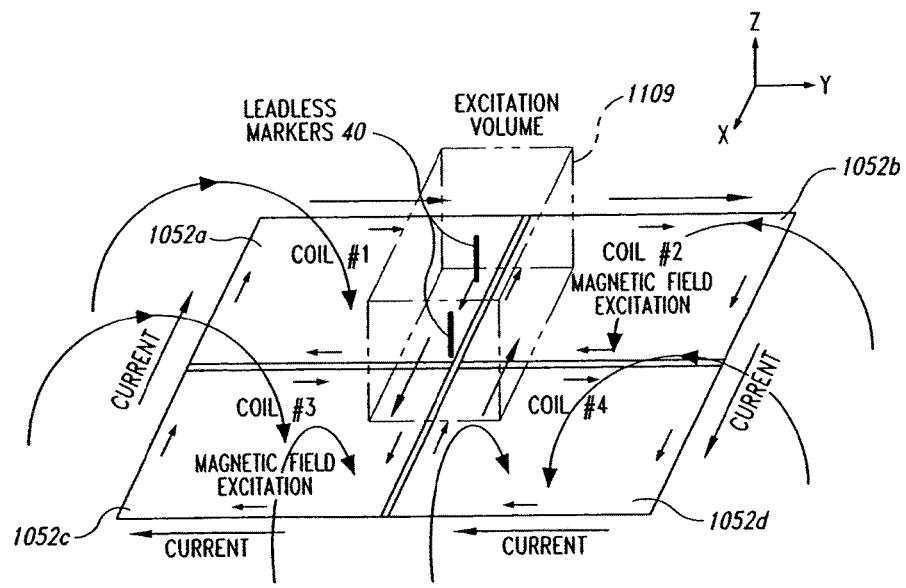
FIG. 22 is a schematic view of an array of coplanar source coils illustrating a magnetic excitation field for energizing markers in a second spatial orientation.

FIG. 22 further illustrates the ability to spatially adjust the excitation field in a manner that energizes any of the markers 40 at different spatial orientations. In this embodiment, the switching network 1044 (FIG. 17) is configured so that the phases of the alternating electrical signals provided to the source coils 1052*a-d* are similar to the configuration shown in FIG. 18. This produces an excitation field with a magnetic moment in the Z direction that energizes markers 40 with longitudinal axes parallel to the Z-axis.

The spatial configuration of the excitation field in the excitation volume 1109 can be quickly adjusted by manipulating the switching network to change the phases of the electrical signals provided to the source coils 1052*a-d*. As a result, the overall magnetic excitation field can be changed to be oriented in either the X, Y or Z directions within the excitation volume 1109. This adjustment of the spatial orientation of the excitation field reduces or eliminates blind spots in the excitation volume 1109. Therefore, the markers 40 within the excitation volume 1109 can be energized by the source coils 1052*a-d* regardless of the spatial orientations of the leadless markers.

In one embodiment, the excitation source 1010 is coupled to the sensor assembly 1012 so that the switching network 1044 (FIG. 17) adjusts orientation of the pulsed generation of the excitation field along the X, Y, and Z axes depending upon the strength of the signal received by the sensor assembly. If the location signal from a marker 40 is insufficient, the switching network 1044 can automatically change the spatial orientation of the excitation field during a subsequent pulsing of the source coils 1052*a-d* to generate an excitation field with a moment in the direction of a different axis or between axes. The switching network 1044 can be manipulated until the sensor assembly 1012 receives a sufficient location signal from the marker.

The excitation source 1010 illustrated in FIG. 17 alternately energizes the source coils 1052*a-d* during an excitation phase to power the markers 40, and then actively de-energizes the source coils 1052*a-d* during a sensing phase in which the sensor assembly 1012 senses the decaying location signals wirelessly transmitted by the markers 40. To actively energize and de-energize the source coils 1052*a-d*, the switching network 1044 is configured to alternatively transfer stored energy from the energy storage device 1042 to the source coils 1052*a-d*, and to then re-transfer energy from the source coils 1052*a-d* back to the energy storage device 1042. The switching network 1044 alternates between first and second "on" positions so that the voltage across the source coils 1052 alternates between positive and negative polarities. For example, when the switching network 1044 is switched to the first "on" position, the energy in the energy storage device 1042 flows to the source coils 1052*a-d*. When the switching network 1044 is switched to the second "on" position, the polarity is reversed such that the energy in the source coils 1052*a-d* is actively drawn from the source coils 1052*a-d* and directed back to the energy storage device 1042. As a result, the energy in the source coils 1052*a-d* is quickly transferred back to the energy storage device 1042 to abruptly terminate the excitation field transmitted from the source coils 1052*a-d* and to conserve power consumed by the energy storage device 1042. This removes the excitation energy from the environment so that the sensor assembly 1012 can sense the location signals from the markers 40 without interference from the significantly larger excitation energy from the excitation source 1010. Several additional details of the excitation source 1010 and alternate embodiments are disclosed in U.S. patent application Ser. No. 10/213,980 filed on Aug. 7, 2002, which is incorporated by reference herein in its entirety.

b. Sensor Assemblies

Figure 23A:
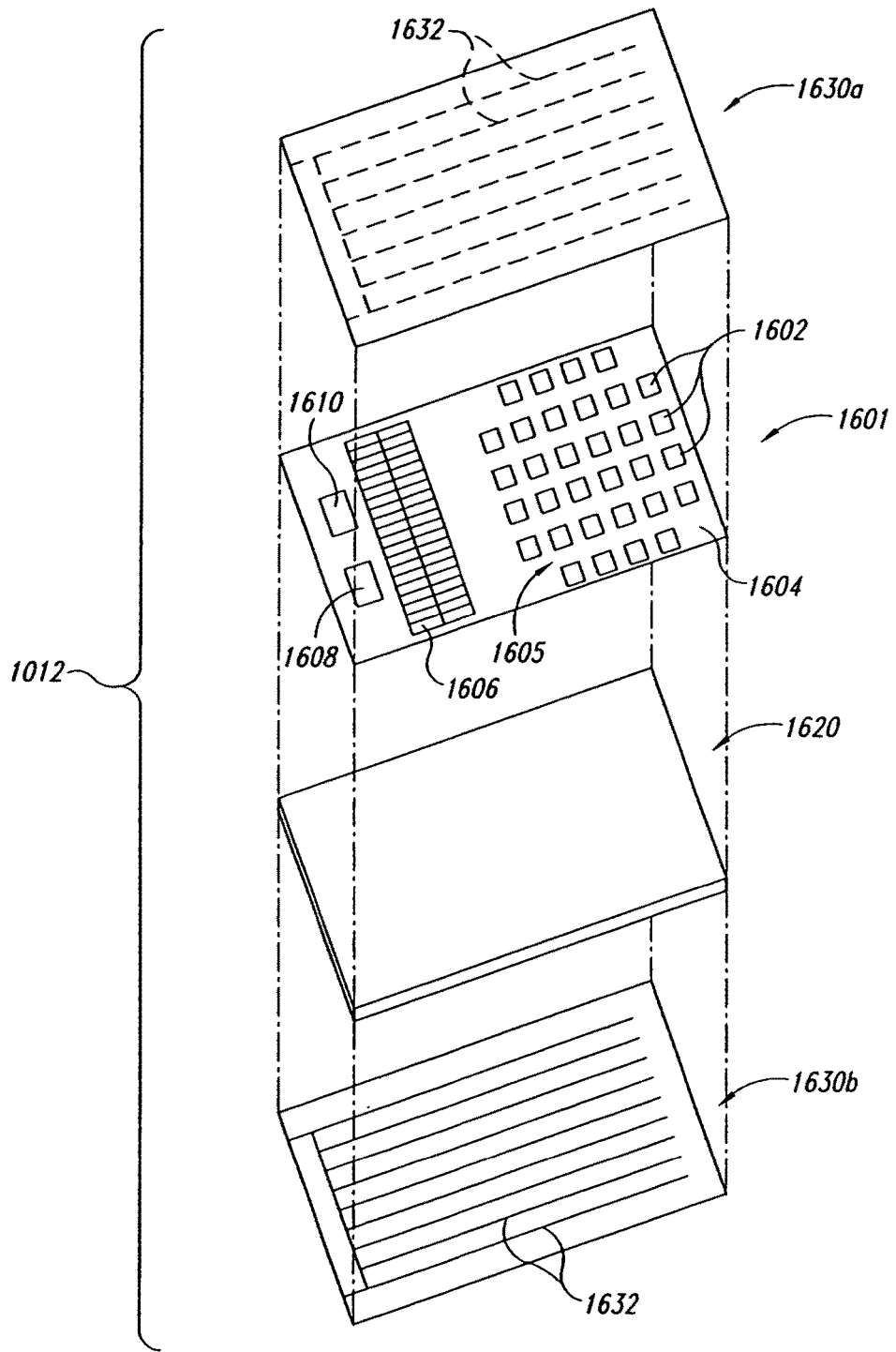
FIG. 23A is an exploded isometric view showing individual components of a sensor assembly for use with a localization system in accordance with an embodiment of the invention.

FIG. 23A is an exploded isometric view showing several components of the sensor assembly 1012 for use in the localization system 1000 (FIG. 17). The sensor assembly 1012 includes a sensing unit 1601 having a plurality of coils 1602 formed on or carried by a panel 1604. The coils 1602 can be field sensors or magnetic flux sensors arranged in a sensor array 1605.

The panel 1604 may be a substantially non-conductive material, such as a sheet of KAPTON® produced by DuPont. KAPTON® is particularly useful when an extremely stable, tough, and thin film is required (such as to avoid radiation beam contamination), but the panel 1604 may be made from other materials and have other configurations. For example, FR4 (epoxy-glass substrates), GETEK or other Teflon-based substrates, and other commercially available materials can be used for the panel 1604. Additionally, although the panel 1604 may be a flat, highly planar structure, in other embodiments, the panel may be curved along at least one axis. In either embodiment, the field sensors (e.g., coils) are arranged in a locally planar array in which the plane of one field sensor is at least substantially coplanar with the planes of adjacent field sensors. For example, the angle between the plane defined by one coil relative to the planes defined by adjacent coils can be from approximately 0° to 10°, and more generally is less than 5°. In some circumstances, however, one or more of the coils may be at an angle greater than 10° relative to other coils in the array.

The sensor assembly 1012 shown in FIG. 23A can optionally include a core 1620 laminated to the panel 1604. The core 1620 can be a support member made from a rigid material, or the core 1620 can be a low density foam, such as a closed-cell Rohacell foam. The core 1620 is preferably a stable layer that has a low coefficient of thermal expansion so that the shape of the sensor assembly 1012 and the relative orientation between the coils 1602 remain within a defined range over an operating temperature range.

The sensor assembly 1012 can further include a first exterior cover 1630*a* on one side of the sensing subsystem and a second exterior cover 1630*b* on an opposing side. The first and second exterior covers 1630*a*-*b* can be thin, thermally stable layers, such as Kevlar or Thermount films. Each of the first and second exterior covers 1630*a*-*b* can include electric shielding 1632 to block undesirable external electric fields from reaching the coils 1602. The electric shielding 1632 can be a plurality of parallel legs of gold-plated, copper strips to define a comb-shaped shield in a configuration commonly called a Faraday shield. It will be appreciated that the shielding can be formed from other materials that are suitable for shielding. The electric shielding can be formed on the first and second exterior covers using printed circuit board manufacturing technology or other techniques.

The panel 1604 with the coils 1602 is laminated to the core 1620 using a pressure sensitive adhesive or another type of adhesive. The first and second exterior covers 1630*a*-*b* are similarly laminated to the assembly of the panel 1604 and the core 1620. The laminated assembly forms a rigid structure that fixedly retains the arrangement of the coils 1602 in a defined configuration over a large operating temperature range. As such, the sensor assembly 1012 does not substantially deflect across its surface during operation. The sensor assembly 1012, for example, can retain the array of coils 1602 in the fixed position with a deflection of no greater than ±0.5 mm, and in some cases no more than ±0.3 mm. The stiffness of the sensing subsystem provides very accurate and repeatable monitoring of the precise location of leadless markers in real time.

In still another embodiment, the sensor assembly 1012 can further include a plurality of source coils that are a component of the excitation source 1010. One suitable array combining the sensor assembly 1012 with source coils is disclosed in U.S. patent application Ser. No. 10/334,700, entitled PANEL-TYPE SENSOR/SOURCE ARRAY ASSEMBLY, filed on Dec. 30, 2002, which is herein incorporated by reference.

Figure 23B:
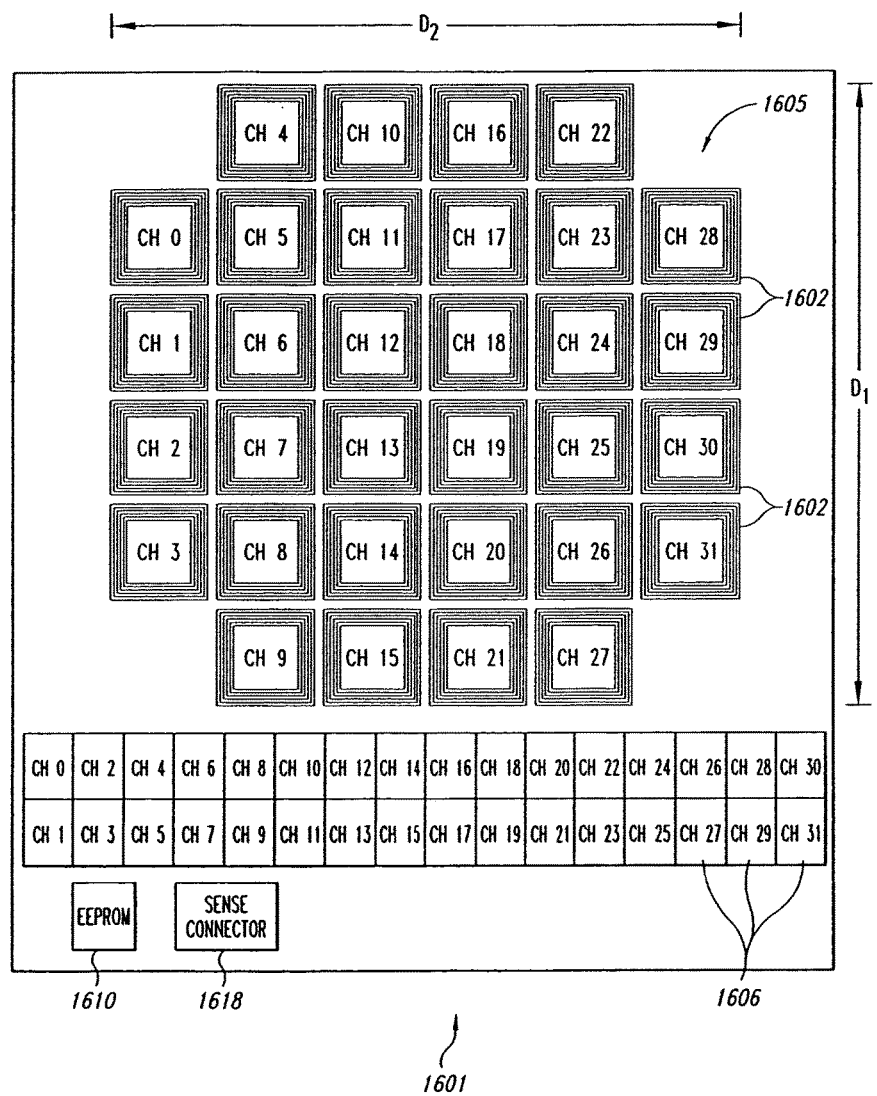
FIG. 23B is a top plan view of a sensing unit for use in the sensor assembly of FIG. 23A.

FIG. 23B further illustrates an embodiment of the sensing unit 1601. In this embodiment, the sensing unit 1601 includes 32 sensor coils 1602; each coil 1602 is associated with a separate channel 1606 (shown individually as channels "Ch 0" through "Ch 31"). The overall dimension of the panel 1604 can be approximately 40 cm by 54 cm, but the array 1605 has a first dimension D1 of approximately 40 cm and a second dimension D2 of approximately 40 cm. The array 1605 can have other sizes or other configurations (e.g., circular) in alternative embodiments. Additionally, the array 1605 can have more or fewer coils, such as 8-64 coils; the number of coils may moreover be a power of 2.

The coils 1602 may be conductive traces or depositions of copper or another suitably conductive metal formed on the panel 1604. Each coil 1602 has a trace with a width of approximately 0.15 mm and a spacing between adjacent turns within each coil of approximately 0.13 mm. The coils 1602 can have approximately 15 to 90 turns, and in specific applications each coil has approximately 40 turns. Coils with less than 15 turns may not be sensitive enough for some applications, and coils with more than 90 turns may lead to excessive voltage from the source signal during excitation and excessive settling times resulting from the coil's lower self-resonant frequency. In other applications, however, the coils 1602 can have less than 15 turns or more than 90 turns.

As shown in FIG. 23B, the coils 1602 are arranged as square spirals, although other configurations may be employed, such as arrays of circles, interlocking hexagons, triangles, etc. Such square spirals utilize a large percentage of the surface area to improve the signal to noise ratio. Square coils also simplify design layout and modeling of the array compared to circular coils; for example, circular coils could waste surface area for linking magnetic flux from the markers 40. The coils 1602 have an inner dimension of approximately 40 mm, and an outer dimension of approximately 62 mm, although other dimensions are possible depending upon applications. Sensitivity may be improved with an inner dimension as close to an outer dimension as possible given manufacturing tolerances. In several embodiments, the coils 1602 are identical to each other or at least configured substantially similarly.

The pitch of the coils 1602 in the array 1605 is a function of, at least in part, the minimum distance between the marker and the coil array. In one embodiment, the coils are arranged at a pitch of approximately 67 mm. This specific arrangement is particularly suitable when the wireless markers 40 are positioned approximately 7-27 cm from the sensor assembly 1012. If the wireless markers are closer than 7 cm, then the sensing subsystem may include sensor coils arranged at a smaller pitch. In general, a smaller pitch is desirable when wireless markers are to be sensed at a relatively short distance from the array of coils. The pitch of the coils 1602, for example, is approximately 50%-200% of the minimum distance between the marker and the array.

In general, the size and configuration of the array 1605 and the coils 1602 in the array depend on the frequency range in which they are to operate, the distance from the markers 40 to the array, the signal strength of the markers, and several other factors. Those skilled in the relevant art will readily recognize that other dimensions and configurations may be employed depending, at least in part, on a desired frequency range and distance from the markers to the coils.

The array 1605 is sized to provide a large aperture to measure the magnetic field emitted by the markers. It can be particularly challenging to accurately measure the signal emitted by an implantable marker that wirelessly transmits a marker signal in response to a wirelessly transmitted energy source because the marker signal is much smaller than the source signal and other magnetic fields in a room (e.g., magnetic fields from CRTs, etc.). The size of the array 1605 can be selected to preferentially measure the near field of the marker while mitigating interference from far field sources. In one embodiment, the array 1605 is sized to have a maximum dimension D1 or D2 across the surface of the area occupied by the coils that is approximately 100% to 300% of a predetermined maximum sensing distance that the markers are to be spaced from the plane of the coils. Thus, the size of the array 1605 is determined by identifying the distance that the marker is to be spaced apart from the array to accurately measure the marker signal, and then arrange the coils so that the maximum dimension of the array is approximately 100% to 300% of that distance. The maximum dimension of the array 1605, for example, can be approximately 200% of the sensing distance at which a marker is to be placed from the array 1605. In one specific embodiment, the marker 40 has a sensing distance of 20 cm and the maximum dimension of the array of coils 1602 is between 20 cm and 60 cm, and more specifically 40 cm.

A coil array with a maximum dimension as set forth above is particularly useful because it inherently provides a filter that mitigates interference from far field sources. As such, one aspect of several embodiments of the invention is to size the array based upon the signal from the marker so that the array preferentially measures near field sources (i.e., the field generated by the marker) and filters interference from far field sources.

The coils 1602 are electromagnetic field sensors that receive magnetic flux produced by the wireless markers 40 and in turn produce a current signal representing or proportional to an amount or magnitude of a component of the magnetic field through an inner portion or area of each coil. The field component is also perpendicular to the plane of each coil 1602. Each coil represents a separate channel, and thus each coil outputs signals to one of 32 output ports 1606. A preamplifier, described below, may be provided at each output port 1606. Placing preamplifiers (or impedance buffers) close to the coils minimizes capacitive loading on the coils, as described herein. Although not shown, the sensing unit 1601 also includes conductive traces or conductive paths routing signals from each coil 1602 to its corresponding output port 1606 to thereby define a separate channel. The ports in turn are coupled to a connector 1608 formed on the panel 1604 to which an appropriately configured plug and associated cable may be attached.

The sensing unit 1601 may also include an onboard memory or other circuitry, such as shown by electrically erasable programmable read-only memory (EEPROM) 1610. The EEPROM 1610 may store manufacturing information such as a serial number, revision number, date of manufacture, and the like. The EEPROM 1610 may also store per-channel calibration data, as well as a record of run-time. The run-time will give an indication of the total radiation dose to which the array has been exposed, which can alert the system when a replacement sensing subsystem is required.

Although shown in one plane only, additional coils or electromagnetic field sensors may be arranged perpendicular to the panel 1604 to help determine a three-dimensional location of the wireless markers 40. Adding coils or sensors in other dimensions could increase the total energy received from the wireless markers 40, but the complexity of such an array would increase disproportionately. The inventors have found that three-dimensional coordinates of the wireless markers 40 may be found using the planar array shown in FIG. 23A-B.

Implementing the sensor assembly 1012 may involve several considerations. First, the coils 1602 may not be presented with an ideal open circuit. Instead, they may well be loaded by parasitic capacitance due largely to traces or conductive paths connecting the coils 1602 to the preamplifiers, as well as a damping network (described below) and an input impedance of the preamplifiers (although a low input impedance is preferred). These combined loads result in current flow when the coils 1602 link with a changing magnetic flux. Any one coil 1602, then, links magnetic flux not only from the wireless marker 40, but also from all the other coils as well. These current flows should be accounted for in downstream signal processing.

A second consideration is the capacitive loading on the coils 1602. In general, it is desirable to minimize the capacitive loading on the coils 1602. Capacitive loading forms a resonant circuit with the coils themselves, which leads to excessive voltage overshoot when the excitation source 1010 is energized. Such a voltage overshoot should be limited or attenuated with a damping or "snubbing" network across the coils 1602. A greater capacitive loading requires a lower impedance damping network, which can result in substantial power dissipation and heating in the damping network.

Another consideration is to employ preamplifiers that are low noise. The preamplification can also be radiation tolerant because one application for the sensor assembly 1012 is with radiation therapy systems that use linear accelerators (LINAC). As a result, PNP bipolar transistors and discrete elements may be preferred. Further, a DC coupled circuit may be preferred if good settling times cannot be achieved with an AC circuit or output, particularly if analog to digital converters are unable to handle wide swings in an AC output signal.

Figure 24:
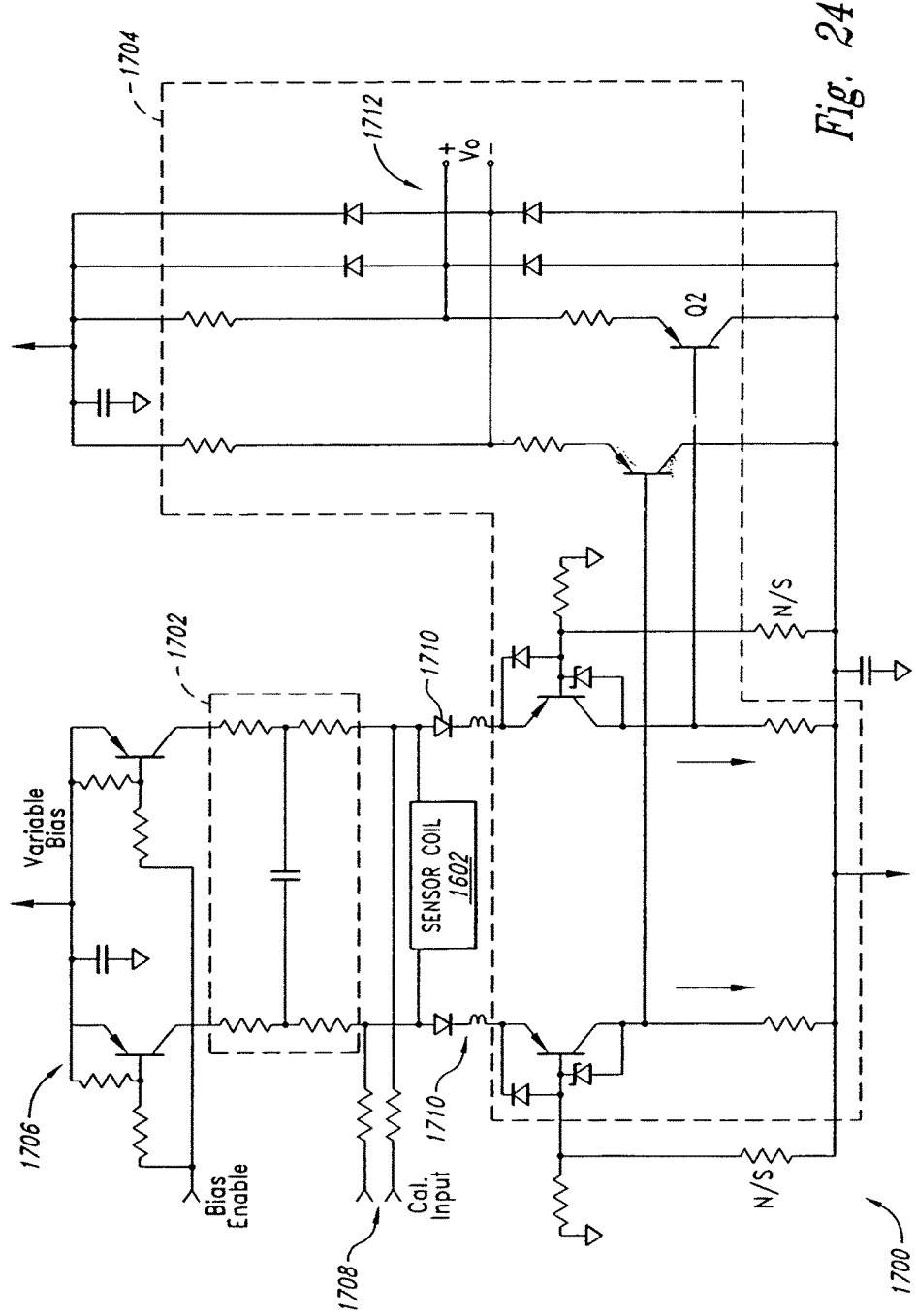
FIG. 24 is a schematic diagram of a preamplifier for use with the sensor assembly of FIG. 23A.

FIG. 24, for example, illustrates an embodiment of a snubbing network 1702 having a differential amplifier 1704. The snubbing network 1702 includes two pairs of series coupled resistors and a capacitor bridging therebetween. A biasing circuit 1706 allows for adjustment of the differential amplifier, while a calibration input 1708 allows both input legs of the differential amplifier to be balanced. The coil 1602 is coupled to an input of the differential amplifier 1704, followed by a pair of high voltage protection diodes 1710. DC offset may be adjusted by a pair of resistors coupled to bases of the input transistors for the differential amplifier 1704 (shown as having a zero value). Additional protection circuitry is provided, such as ESD protection diodes 1712 at the output, as well as filtering capacitors (shown as having a 10 nF value).

c. Signal Processors and Controllers

The signal processor 1014 and the controller 1016 illustrated in FIG. 17 receive the signals from the sensor assembly 1012 and calculate the absolute positions of the markers 40 within the reference frame. Suitable signal processing systems and algorithms are set forth in U.S. application Ser. Nos. 10/679,801; 10/749,478; 10/750,456; 10/750,164; 10/750,165; 10/749,860; and 10/750,453, all of which are incorporated herein by reference.

EXAMPLE

Overview

Figure 25:
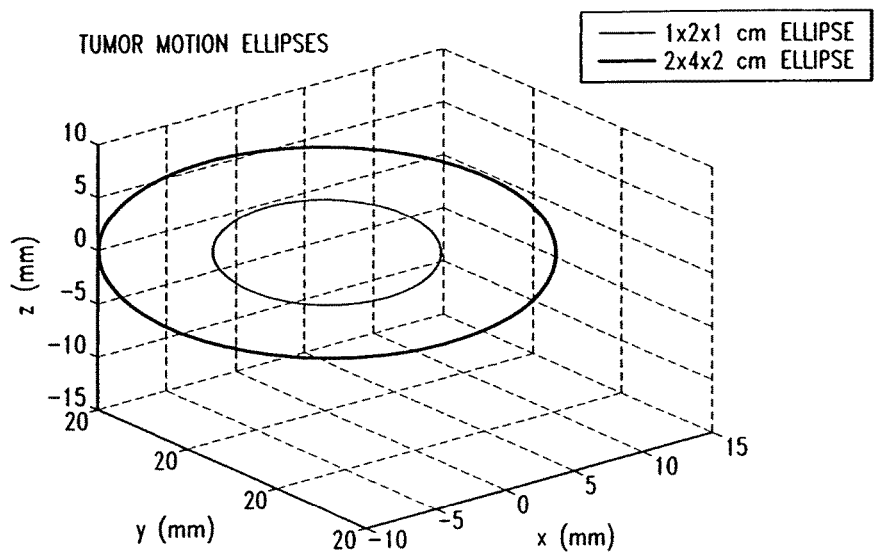
FIG. 25 is a graph of illustrative tumor motion ellipses from experimental phantom based studies of the system.

An experimental phantom based study was conducted to determine effectiveness of this system for real-time tracking. In this experiment, a custom 4D stage was constructed to allow arbitrary motion in three axes for speeds up to 10 cm/sec in each dimension, with accuracy to 0.3 mm. Position accuracy was measured by a 3D digitizing arm attached to the stage system. As shown in FIG. 25, two ellipses were created with peak to peak motion of 2 cm, 4 cm and 2 cm; and 1 cm by 2 cm and 1 cm in the x, y and z direction respectively. Three periods were used to correspond to 15, 17 and 20 breaths per minute. A single transponder was used with an integration time of 33 ms, 67 ms and 100 ms and two transponders were used with integration times of 67 ms and 100 ms. The transponders were placed in a custom phantom mounted to the 4D stage. The experiment was performed with the isocenter placed 14 cm from the AC magnetic array to simulate the position of an average lung cancer patient. The 4D stage ran each trajectory while the real tracking system measured the transponder positions. Measured position was compared against the phantom position. The effects of ellipse size, speed, transponder number and integration time were characterized.

Experiment Summary

Figure 26:
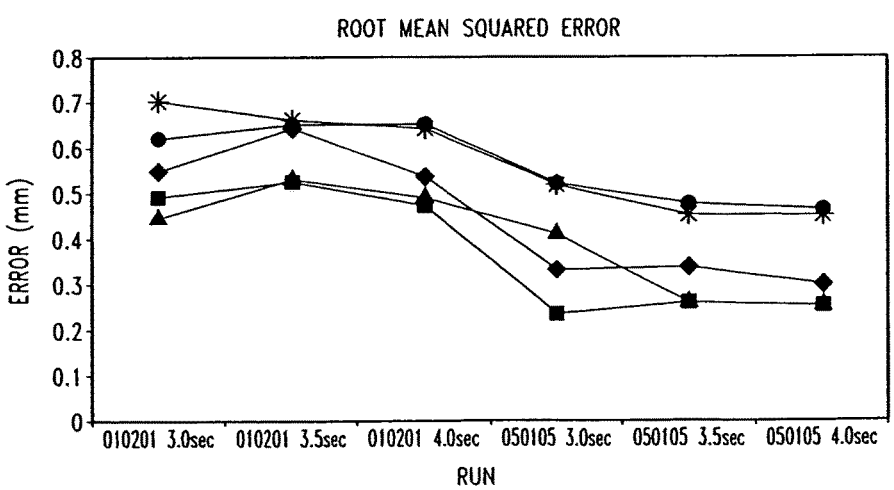
FIG. 26 is a graph of root mean square (RMS) error from experimental phantom based studies of the system.
Figure 27:
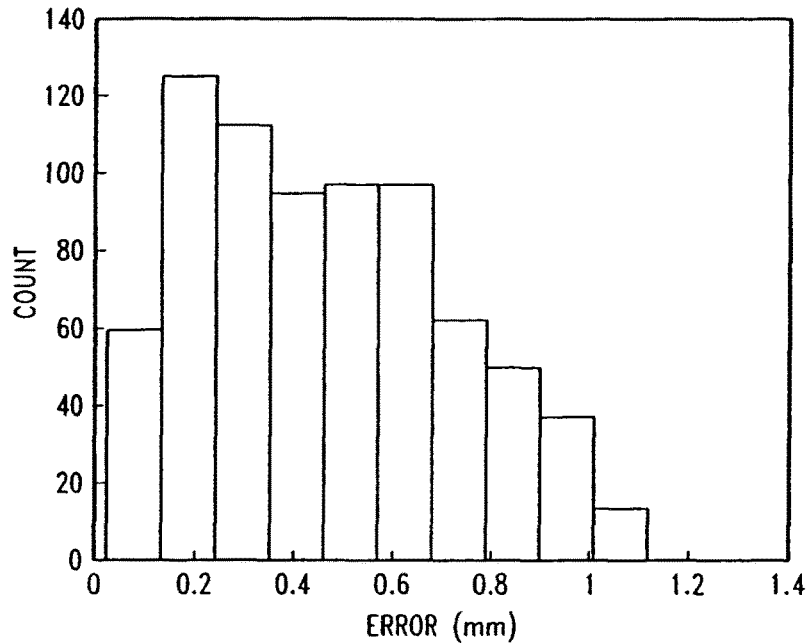
FIG. 27 is an exemplary histogram of localization error from experimental phantom based studies of the system.
Figure 28:
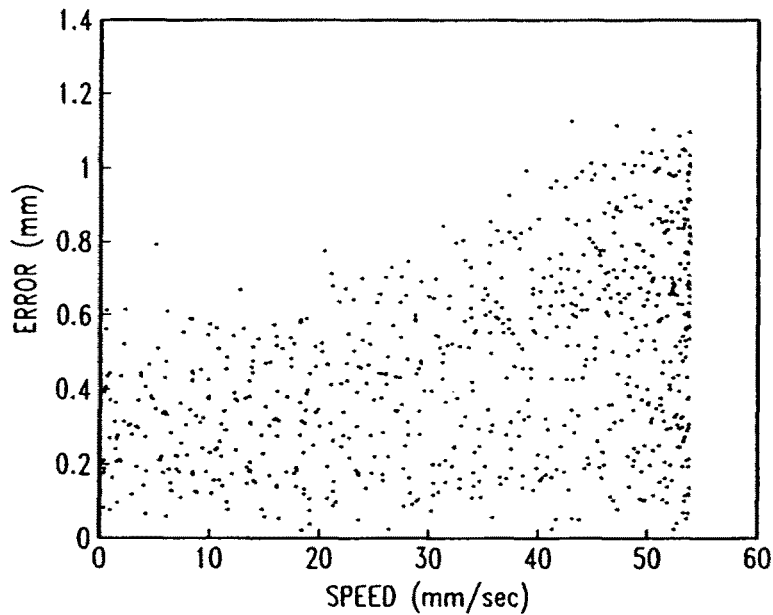
FIG. 28 is graph of position error as a function of speed from experimental phantom based studies of the system.

As shown in FIG. 26, the root mean square (RMS) error was less than 1 mm for each ellipse, period and transponder integration time. The system was able to track points throughout the path of the ellipse, for example, in a trajectory of a large ellipse moving at 17 breaths per minute. FIG. 27 is a histogram of localization errors illustrating that the range of error was low for each point measured. As shown in FIG. 28, the RMS error was higher in areas of increased velocity in most trajectories. With respect to this experiment, a single transponder system performed slightly better than dual transponder systems, with the best system being a single transponder with a 67 ms integration time.

CONCLUSION

The above description of illustrated embodiments, including what is described in the Abstract, is not intended to be exhaustive or to limit the invention to the precise forms disclosed. Although specific embodiments of and examples are described herein for illustrative purposes, various equivalent modifications can be made without departing from the spirit and scope of the invention, as will be recognized by those skilled in the relevant art. The teachings provided herein of the invention can be applied to target locating and tracking systems, not necessarily the exemplary system generally described above.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the invention can be modified, if necessary, to employ systems, devices and concepts of the various patents, applications and publications to provide yet further embodiments of the invention.

These and other changes can be made to the invention in light of the above-detailed description. In general, in the following claims, the terms used should not be construed to limit the invention to the specific embodiments disclosed in the specification and the claims, but should be construed to include all target locating and monitoring systems that operate in accordance with the claims to provide apparatus and methods for locating, monitoring, and/or tracking the position of a selected target within a body. Accordingly, the invention is not limited, except as by the appended claims.

We claim:

1. A method of treating a target in a lung of a patient, comprising:
   positioning a leadless marker in the lung of the patient relative to the target;
   collecting position data of the implanted marker with a localization system using a non-ionizing energy to track the implanted marker while the patient is in a treatment session;
   determining the location of the implanted marker in an external reference frame based on the collected position data;
   providing an objective output in the external reference frame that is (a) directly responsive to movement of the implanted marker and (b) provided at a periodicity that tracks the location of the target;
   wherein the position data is collected at a time $t_n$, and wherein providing the objective output responsive to the location of the target comprises providing the objective output to at least one of a user interface, a memory device, a computer and a medical device within a latency period, wherein the position data is collected by the localization system; and
   wherein the latency period between the movement of the implanted marker and the objective output of the collected position data during application of therapeutic ionizing radiation is not greater than approximately 2 seconds of time $t_n$, and the objective output is provided at a periodicity not greater than approximately 2 seconds during the application of the therapeutic ionizing radiation.

2. The method of claim 1, further comprising:
   positioning the target at a desired situs in an external reference frame of a radiation delivery device using the objective output; and
   irradiating the patient with a radiation beam of the radiation delivery device.

3. The method of claim 2, further comprising controlling the radiation delivery device to activate the radiation beam when the determined location of the marker indicates that the target is at the desired situs and deactivating the radiation beam when the determined location of the marker indicates that the target is outside of the desired situs.

4. The method of claim 2, further comprising controlling the radiation delivery device by moving a robot based on the determined location of the marker.

5. The method of claim 2, further comprising controlling the radiation device by articulating the position of the beam based on the determined location of the marker.

6. The method of claim 2, further comprising controlling the shape of the beam based on the determined location of the marker.

7. The method of claim 1, further comprising moving a surgical instrument relative to the target while tracking the target using the objective output.

8. The method of claim 7 wherein the surgical instrument comprises a knife and the method further comprises cutting and removing a portion of the lung of the patient.

9. The method of claim 7 wherein the surgical instrument comprises an ablation device and the method further comprises ablating a portion of the lung.

10. The method of claim 7 wherein the surgical instrument comprises a cryogenic device and the method further comprises cryogenically necrosing cells.

11. The method of claim 1 wherein positioning the leadless marker comprises deploying the marker in the lung by inserting a catheter into the lung and releasing the marker from the catheter.

12. The method of claim 11 wherein inserting the catheter comprises guiding the catheter through a lumen of the lung, and wherein releasing the marker comprises anchoring the marker in the lung.

13. The method of claim 11 wherein inserting the catheter comprises piercing a lumen in a respiratory system.

14. The method of claim 1 wherein positioning the marker comprises passing a needle through the thorax of the patient and releasing the marker from the needle into the lung of the patient.

15. The method of claim 1 wherein positioning the marker comprises surgically attaching the marker to the lung.

16. The method of claim 1, further comprising repeating the collecting, determining and providing procedures to monitor the position of the marker within the lung.

17. The method of claim 1 wherein the latency period is not greater than approximately 200 ms of time $t_n$ and at a periodicity not greater than approximately 200 ms.

18. The method of claim 1 wherein the latency period is not greater than approximately 100 ms of time $t_n$ and at a periodicity not greater than approximately 100 ms.

19. The method of claim 1, further comprising deploying the leadless marker by optically guiding a delivery device through the patient and releasing the marker at a desired site.

20. The method of claim 1, further comprising deploying the leadless marker in the patient by fluoroscopically guiding a delivery device through the patient and releasing the marker at a desired site.

21. The method of claim 1, further comprising deploying the leadless marker in the patient by magnetically guiding a delivery device through the patient and releasing the marker at a desired site.

* * * * *